United States Patent
Bremer et al.

(10) Patent No.: US 6,541,081 B1
(45) Date of Patent: Apr. 1, 2003

(54) ESTER COMPOUNDS AND THEIR USE IN LIQUID-CRYSTALLINE MEDIA

(75) Inventors: Matthias Bremer, Darmstadt (DE); Michael Heckmeier, Bensheim (DE); Joachim Krause, Dieburg (DE); Brigitte Schuler, Haibach (DE); Achim Götz, Alsbach-Hähnlein (DE)

(73) Assignee: Merck Patent Gesellschaft mit beschränkter Haftung, Darmstadt (DE)

( * ) Notice: Subject to any disclaimer, the term of this patent is extended or adjusted under 35 U.S.C. 154(b) by 88 days.

(21) Appl. No.: 09/712,134

(22) Filed: Nov. 15, 2000

(30) Foreign Application Priority Data

Nov. 16, 1999 (DE) .......................... 199 54 906

(51) Int. Cl.[7] .................. C09K 19/20; C09K 19/30; C09K 19/12
(52) U.S. Cl. .............. 428/1.1; 252/299.63; 252/299.64; 252/299.65; 252/299.66; 252/299.67
(58) Field of Search ....................... 252/299.63, 299.67, 252/299.66, 299.64, 299.65; 428/1.1

(56) References Cited

U.S. PATENT DOCUMENTS 4,705,884 A * 11/1987 Matsumoto et al. ........ 560/109
5,922,243 A * 7/1999 Matsui et al. .......... 252/299.67

OTHER PUBLICATIONS

CAPLUS 1977: 155559.*
CAPLUS 1981: 578970.*
CAPLUS 1994: 310732.*

* cited by examiner

Primary Examiner—Shean C. Wu
(74) Attorney, Agent, or Firm—Millen, White, Zelano & Branigan, P.C.

(57) ABSTRACT

The invention relates to esters of the formula I and to a liquid-crystalline medium based on a mixture of polar compounds having positive dielectric anisotropy, characterized in that it comprises one or more compounds of the general formula I

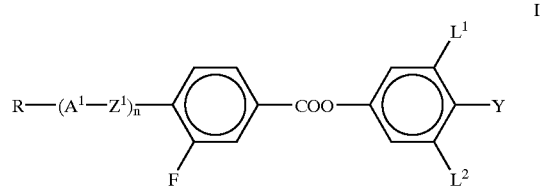

in which R, $A^1$, $Z^1$, $L^1$, $L^2$, Y and n are as defined in herein.

20 Claims, No Drawings

ESTER COMPOUNDS AND THEIR USE IN LIQUID-CRYSTALLINE MEDIA

The present invention relates to ester compounds of the formula I and their use in a liquid-crystalline medium.

Liquid crystals are used, in particular, as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a twisted nematic structure, STN (supertwisted nematic) cells, SBE (superbirefringence effect) cells and OMI (optical mode interference) cells. The most common display devices are based on the Schadt-Helfrich effect and have a twisted nematic structure.

The liquid-crystal materials must have good chemical and thermal stability and good stability to electric fields and electromagnetic radiation. Furthermore, the liquid-crystal materials should have low viscosity and give short addressing times, low threshold voltages and high contrast in the cells.

They should furthermore have a suitable mesophase, for example a nematic or cholesteric mesophase for the above-mentioned cells, at conventional operating temperatures, i.e. in the broadest possible range above and below room temperature. Since liquid crystals are generally used as mixtures of a plurality of components, it is important that the components are readily miscible with one another. Further properties, such as the electrical conductivity, the dielectric anisotropy and the optical anisotropy, must satisfy various requirements depending on the cell type and area of application. For example, materials for cells having a twisted nematic structure should have positive dielectric anisotropy and low electrical conductivity.

For example, media having large positive dielectric anisotropy, broad nematic phases, relatively low birefringence, very high resistivity, good UV and temperature stability and low vapour pressure are desired for matrix liquid-crystal displays containing integrated non-linear elements for switching individual pixels (MLC displays).

Matrix liquid-crystal displays of this type are known. Non-linear elements which can be used for individual switching of the individual pixels are, for example, active elements (i.e. transistors). This is then referred to as an "active matrix", and a distinction can be made between two types:

1. MOS (metal oxide semiconductor) or other diodes on a silicon wafer as substrate.
2. Thin-film transistors (TFTs) on a glass plate as substrate.

The use of single-crystal silicon as substrate material limits the display size, since even modular assembly of various part-displays results in problems at the joints.

In the case of more promising type 2, which is preferred, the electro-optical effect used is usually the TN effect. A distinction is made between two technologies: TFTs comprising compound semiconductors, for example CdSe, or TFTs based on polycrystalline or amorphous silicon. Intensive work is being carried out worldwide on the latter technology.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be expanded to fully colour-compatible displays, in which a mosaic of red, green and blue filters is arranged in such a way that each filter element is located opposite a switchable pixel.

The TFT displays usually operate as TN cells with crossed polarizers in transmission and are backlit.

The term MLC displays here covers any matrix display containing integrated non-linear elements, i.e., besides the active matrix, also displays containing passive elements, such as varistors or diodes (MIM=metal-insulator-metal).

MLC displays of this type are particularly suitable for TV applications (for example pocket TVs) or for high-information displays for computer applications (lap-tops) and in automobile or aircraft construction. Besides problems regarding the angle dependence of the contrast and the response times, difficulties also arise in MLC displays due to inadequate resistivity of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210–288 Matrix LCD Controlled by Double Stage Diode Rings, p. 141 ff, Paris; STROMER, M., Proc. Eurodisplay 84, September 1984: Design of Thin Film Transistors for Matrix Addressing of Television Liquid Crystal Displays, p. 145 ff, Paris]. With decreasing resistance, the contrast of an MLC display drops, and the problem of after-image elimination can occur. Since the resistivity of the liquid-crystal mixture generally drops over the life of an MLC display owing to interaction with the interior surfaces of the display, a high (initial) resistance is very important in order to obtain acceptable service lives. In particular in the case of low-volt mixtures, it was hitherto impossible to achieve very high resistivity values. It is furthermore important that the resistivity increases as little as possible with increasing temperature and after heating and/or UV exposure. The low-temperature properties of the mixtures of the prior art are also particularly disadvantageous. It is required that crystallization and/or smectic phases do not occur, even at low temperatures, and that the temperature dependence of the viscosity is as low as possible. The MLC displays of the prior art thus do not satisfy today's requirements.

Besides liquid-crystal displays which use backlighting, i.e. are operated transmissively and optionally transflectively, there is also particular interest in reflective liquid-crystal displays. These reflective liquid-crystal displays use the ambient light for information display. They thus consume significantly less energy than backlit liquid-crystal displays of corresponding size and resolution. Since the TN effect is characterized by very good contrast, reflective displays of this type are readily legible even under bright ambient conditions. This is already known of simple reflective TN displays, as used, for example, in wristwatches and pocket calculators. However, the principle can also be applied to high-quality, higher-resolution active matrix addressed displays such as TFT displays. Here, as is already the case in the conventional transmissive TFT-TN displays, the use of liquid crystals of low birefringence ($\Delta n$) is necessary in order to achieve low optical retardation ($d \cdot \Delta n$).

This low optical retardation results in a low viewing angle dependence of the contrast, which is usually acceptable (cf. DE 30 22 818). In reflective displays, the use of liquid crystals of low birefringence is much more important than in transmissive displays, since in reflective displays, the effective layer thickness, through which the light passes, is approximately twice as large as in transmissive displays of the same layer thickness.

Besides the lower power consumption (no need for backlight), other advantages of reflective displays over transmissive displays are the space saving, which results in a very low installation depth, and the reduction in problems arising from temperature gradients resulting from differences in heating caused by the backlight.

There thus continues to be a great demand for MLC displays which have very high resistivity at the same time as a broad operating temperature range, short response times, even at low temperatures, and a low threshold voltage, and which do not have these disadvantages, or only do so to a reduced extent.

In TN (Schadt-Helfrich) cells, media are desired which facilitate the following advantages in the cells:

expanded nematic phase range (in particular down to low temperatures)

switchability at extremely low temperatures (outdoor use, automobile, avionics)

increased resistance to UV radiation (longer life)

lower threshold (addressing) voltage lower birefringence so as to improve the observation angle range.

The media available from the prior art do not allow these advantages to be achieved while simultaneously retaining the other parameters.

In the case of supertwisted (STN) cells, media are desired which enable greater multiplexability and/or lower threshold voltages and/or broader nematic phase ranges (in particular at low temperatures). To this end, a further extension of the parameter latitude available (clearing point, smectic-nematic transition or melting point, viscosity, dielectric parameters, elastic parameters) is urgently desired.

It is an object of the invention to provide media for these MLC, TN or STN displays, in particular for reflective MLC displays, which do not have the abovementioned disadvantages or only do so to a reduced extent, and preferably at the same time have very high resistivity values and low threshold voltages.

Upon further study of the specification and appended claims, further objects and advantages of this invention will become apparent to those skilled in the art.

It has now been found that these objects can be achieved by using media according to the invention in displays. The mixtures of the invention are particularly notable for their excellent low-temperature behaviour.

The invention thus includes a liquid-crystalline medium based on a mixture of polar compounds having positive dielectric anisotropy, characterized in that it comprises one or more compounds of the general formula I

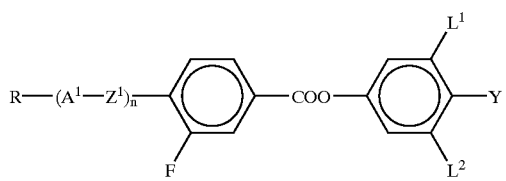

I in which

R is H, an alkyl or alkenyl radical having 1 to 15 carbon atoms which is unsubstituted, monosubstituted by CN or $CF_3$ or at least monosubstituted, upto pehalo-substituted, by halogen, where one or more $CH_2$ groups in these radicals may also, in each case independently of one another, be replaced by —O—, —S—,

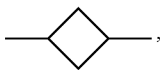

—CO—, —CO—O—, —O—CO— or —O—CO—O— in such a way that O atoms are not linked directly to one another, $A^1$ (a) is a trans-1,4-cyclohexylene radical in which, in addition, one or more non-adjacent $CH_2$ groups may be replaced by —O— and/or —S—, (b) is a 1,4-phenylene radical, in which, in addition, one or two CH groups may be replaced by N, (c) is a 1,4-cyclohexenylene radical, (d) is a radical from the group consisting of 1,4-bicyclo[2.2.2]octylene, piperidine-1,4-diyl, naphthalene-2,6-diyl, decahydro-naphthalene-2,6-diyl and 1,2,3,4-tetra-hydronaphthalene-2,6-diyl, where the radicals (a), (b), (c) and (d) may be mono-substituted or polysubstituted by CN or fluorine, $z^1$ is —COO—, —O—CO—, —$CH_2$O—, —O$CH_2$—, —$C_2H_4$—, —CH=CH—, —$CF_2$O—, —O$CF_2$—, —C≡C—, —$(CH_2)_4$—, —CH=CH$C_2H_4$—, —$C_2F_4$— or a single bond, $L^1$ or $L^2$ are each, independently of one another, H or F, Y is F, Cl, CN or an alkyl or alkoxy radical having 1 to 6 carbon atoms which is substituted by one or more halogen atoms, where one or more $CH_2$ groups may also be replaced by —O— or —CH=CH— in such a way that O atoms are not linked directly to one another, and n is 0, 1 or 2.

The compounds of the formula I, which the invention likewise provides, have a broad range of applications. Depending on the choice of substituents, these compounds can serve as base materials of which liquid-crystalline media are predominantly composed; however, it is also possible to add compounds of the formula I to liquid-crystalline base materials from other classes of compounds in order, for example, to modify the dielectric and/or optical anisotropy of a dielectric of this type and/or to optimize its threshold voltage and/or its viscosity.

In the pure state, the compounds of the formula I are colourless and form liquid-crystalline mesophases in a temperature range which is favourably located for electro-optical use. They are stable chemically, thermally and to light.

Particular preference is given to compounds of the formula I in which Z is a single bond, furthermore —$CH_2$—$CH_2$—. n is preferably 0 or 1, $A^1$ is preferably a cyclohexane ring or a dioxane ring.

Y is preferably F, Cl, CN, $CF_3$, $CF_2H$, $OCF_3$, $OCF_2H$, $OCFHCF_3$, $OCFHCH_2F$, $OCFHCHF_2$, $OCF_2CH_3$, $OCF_2CH_2F$, $OCF_2CHF_2$, $OCF_2CF_2CF_2H$, $OCF_2CF_2CH_2F$, $OCFHCF_2CF_3$, $OCFHCF_2CHF_2$, $OCFHCFHCF_3$, $OCH_2CF_2CF_3$, $OCF_2CF_2CF_3$, $OCF_2CFHCHF_2$, $OCF_2CH_2CHF_2$, $OCFHCF_2CHF_2$, $OCFHCFHCHF_2$, $OCFHCH_2CF_3$, $OCH_2CFHCF_3$, $OCH_2CF_2CHF_2$, $OCF_2CFHCH_3$, $OCF_2CH_2CHF_2$, $OCFHCF_2CH_3$, $OCFHCFHCHF_2$, $OCFHCH_2CF_3$, $OCH_2CF_2CHF_2$, $OCH_2CFHCHF_2$, $OCF_2CH_2CH_3$, $OCFHCFHCH_3$, $OCFHCH_2CHF_2$, $OCH_2CF_2CH_3$, $OCH_2CFHCHF_2$, $OCH_2CH_2CHF_2$, $OCHCH_2CH_3$, $OCH_2CFHCH_3$, $OCH_2CH_2CHF_2$, $OCClFCF_3$, $OCClFCClF_2$, $OCClFCHF_2$, $OCFHCCl_2F$, OCClFCHF$_2$, OCClFCClF$_2$, OCF$_2$CHCl$_2$, OCF$_2$CHCl$_2$, OCF$_2$CCl$_2$F, OCF$_2$CClFH, OCF$_2$CClF$_2$, OCF$_2$CF$_2$CClF$_2$, OCF$_2$CF$_2$CCl$_2$F, OCClFCF$_2$CF$_3$, OCClFCF$_2$CHF$_2$, OCClFCF$_2$CClF$_2$, OCClFCFHCF$_3$, OCClFCClFCF$_3$, OCCl$_2$CF$_2$CF$_3$, OCClHCF$_2$CF$_3$, OCClFCF$_2$CF$_3$, OCClFCClFCF$_3$, OCF$_2$CClFCHF$_2$, OCF$_2$CF$_2$CCl$_2$F, OCF$_2$CCl$_2$CHF$_2$, OCF$_2$CH$_2$CClF$_2$, OCClFCF$_2$CFH$_2$, OCFHCF$_2$CCl$_2$F, OCClFCFHCHF$_2$, OCClFCClFCF$_2$H, OCFHCFHCClF$_2$, OCClFCH$_2$CF$_3$, OCFHCCl$_2$CF$_3$, OCCl$_2$CF$_2$CF$_2$H, OCH$_2$CF$_2$CClF$_2$, OCF$_2$CClFCH$_3$, OCF$_2$CFHCCl$_2$H, OCF$_2$CCl$_2$CFH$_2$, OCF$_2$CH$_2$CCl$_2$F, OCClFCF$_2$CH$_3$, OCFHCF$_2$CCl$_2$H, OCClFCClFCHF$_2$, OCFHCFHCCl$_2$F, OCClFCH$_2$CF$_3$, OCFHCCl$_2$CF$_3$, OCCl$_2$CF$_2$CFH$_2$, OCH$_2$CF$_2$CCl$_2$F, OCCl$_2$CFHCF$_2$H, OCClHCClFCF$_2$H, OCF$_2$CClHCClH$_2$, OCF$_2$CH$_2$CCl$_2$H, OCClFCFHCH$_3$, OCF$_2$CClFCCl$_2$H, OCClFCH$_2$CFH$_2$, OCFHCCl$_2$CFH$_2$, OCCl$_2$CF$_2$CH$_3$, OCH$_2$CF$_2$CClH$_2$, OCCl$_2$CFHCFH$_2$, OCH$_2$CClFCFCl$_2$, OCH$_2$CH$_2$CF$_2$H, OCClHCClHCF$_2$H, OCH$_2$CCl$_2$CF$_2$H, OCClFCH$_2$CH$_3$, OCFHCH$_2$CCl$_2$H, OCClHCFHCClH$_2$, OCH$_2$CFHCCl$_2$H, OCCl$_2$CH$_2$CF$_2$H, OCH$_2$CCl$_2$CF$_2$H, CH=CF$_2$, OCH=CF$_2$, CF=CF$_2$, OCF=CF$_2$, CF=CHF, OCF=CHF, CH=CHF, OCH=CHF in particular F, Cl, CN, CF$_3$, CHF$_2$, OCF$_3$, OCHF$_2$, OCFHCF$_3$, OCFHCHF$_2$, OCFHCHF$_2$, OCF$_2$CH$_3$, OCF$_2$CHF$_2$, OCF$_2$CHF$_2$, OCF$_2$CF$_2$CHF$_2$, OCF$_2$CF$_2$CHF$_2$, OCFHCF$_2$CF$_3$, OCFHCF$_2$CHF$_2$, OCF$_2$CF$_2$CF$_3$, OCF$_2$CF$_2$CClF$_2$, OCClFCF$_2$CF$_3$ or CH=CHF$_2$.

If R is an alkyl radical and/or an alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4-or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R is an alkyl radical in which one CH$_2$ group has been replaced by —CH=CH—, this can be straight-chain or branched. It is preferably straight-chain and has 2 to 10 carbon atoms. Accordingly, it is in particular vinyl, prop-1- or prop-2-enyl, but-1-, -2- or but-3-enyl, pent-1-, -2-, -3- or pent-4-enyl, hex-1-, -2-, -3-, -4- or hex-5-enyl, hept-1-, -2-, -3-, -4-, -5- or hept-6-enyl, oct-1-, -2-, -3-, -4-, -5-, -6- or oct-7-enyl, non-1-, -2-, -3-, -4-, -5-, -6-, -7- or non-8-enyl, dec-1-, -2-, -3-, -4-, -5-, -6-, -7-, -8-or dec-9-enyl.

If R is an alkyl radical in which one CH$_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms. They are accordingly in particular acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R is an alkyl radical in which one CH$_2$ group has been replaced by unsubstituted or substituted —CH=CH— and an adjacent CH$_2$ group has been replaced by CO or CO—O or O—CO, this can be straight-chain or branched. It is preferably straight-chain and has 4 to 13 carbon atoms. Accordingly, they are in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxy-heptyl, 8-methacryloyloxyoctyl or 9-methacryloyloxy-nonyl.

If R is an alkyl or alkenyl radical which is monosubstituted by CN or CF$_3$, this radical is preferably straight-chain. The substitution by CN or CF$_3$ is in any position.

If R is an alkyl or alkenyl radical which is at least monosubstituted by halogen, this radical is preferably straight-chain and halogen is preferably F or Cl. In the case of polysubstitution, halogen is preferably F. The resulting radicals also include perfluorinated radicals. In the case of monosubstitution, the fluoro or chloro substituent can be in any desired position, but is preferably in the ω-position.

Compounds of the formula I which contain pendant groups R which are suitable for polymerization reactions are suitable for the preparation of the liquid-crystalline polymers.

Compounds of the formula I containing branched pendant groups R may occasionally be of importance owing to better solubility in the conventional liquid-crystalline base materials, but in particular as chiral dopants if they are optically active. Smectic compounds of this type are suitable as components for ferro-electric materials.

Compounds of the formula I having $S_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methyl-propoxy, 2-methylbutoxy, 3-methylbutoxy, 2-methyl-pentoxy, 3-methylpentoxy, 2-ethylhexoxy, 1-methylhexoxy or 1-methylheptoxy.

If R is an alkyl radical in which two or more CH$_2$ groups have been replaced by —O— and/or —CO—O—, this can be straight-chain or branched. It is preferably branched and has 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxy-heptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis-(ethoxycarbonyl)ethyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis-(ethoxycarbonyl)ethyl, 3,3-bis(ethoxycarbonyl)propyl, 4,4-bis(ethoxycarbonyl) butyl or 5,5-bis(ethoxy-carbonyl)hexyl.

The compounds of the formula I are prepared by methods known per se, as described in the literature (for example in the standard works, such as Houben-Weyl, Methoden der Organischen Chemie, Georg-Thieme-Verlag, Stuttgart), to be precise under reaction conditions which are known and suitable for said reactions. Use can also be made here of variants which are known per se, but are not mentioned here in greater detail.

The compounds according to the present invention can be prepared, for example, as follows:

The invention also relates to electro-optical displays (in particular STN or MLC displays having two plane-parallel outer plates, which, together with a frame, form a cell, integrated non-linear elements for switching individual pixels on the outer plates, and a nematic liquid-crystal mixture of positive dielectric anisotropy and high resistivity which is located in the cell) which contain media of this type, and to the use of these media for electro-optical purposes.

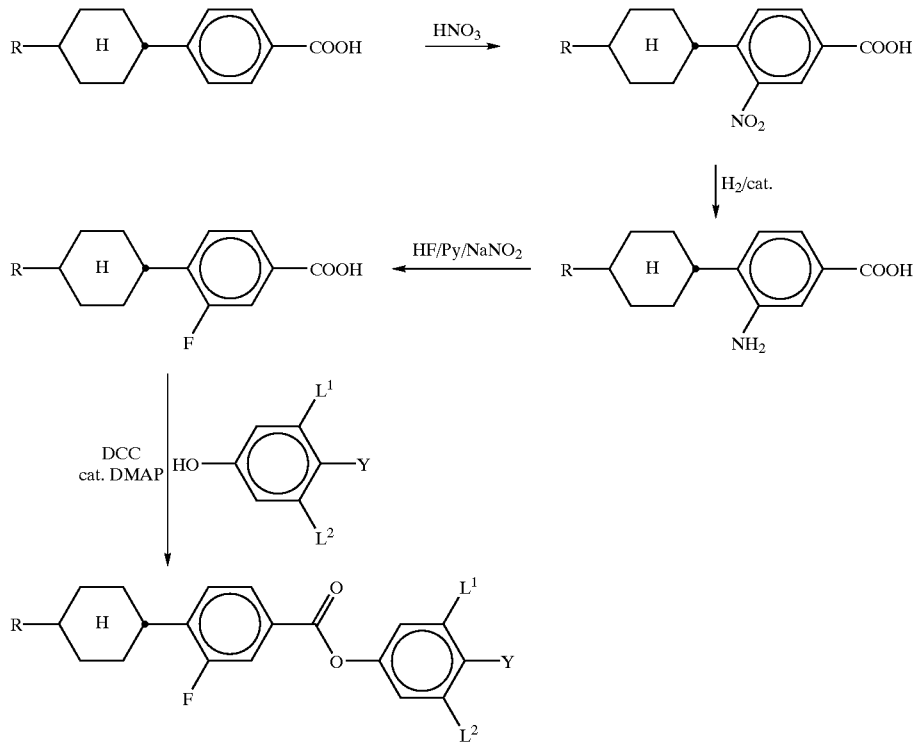

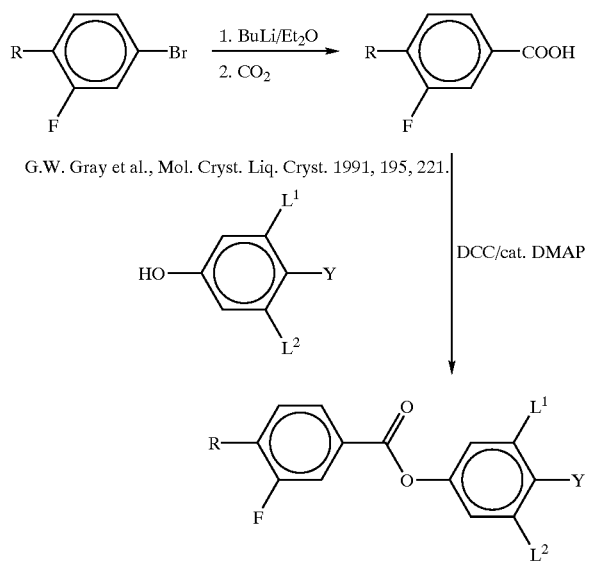

The liquid-crystal mixtures according to the invention allow a significant extension of the parameter latitude which is available.

The achievable combinations of clearing point, viscosity at low temperature, thermal and UV stability and optical anisotropy and treshold voltage are far superior to current prior art materials.

The requirement for a high clearing point, nematic phase at low temperature and simultaneously a low threshold voltage has hitherto only been met inadequately. Although liquid-crystal mixtures such as MLC-6476 and MLC-6625 (Merck KGaA, Darmstadt, Germany) have comparable clearing points and low-temperature stabilities, they have, however, both much higher Δn values of about 0.075 and much higher threshold voltages of about $\geq 1.7$ V.

While maintaining the nematic phase down to $-20°$ C., preferably down to $-30°$ C., particularly preferably down to $-40°$ C., the liquid-crystal mixtures according to the invention allow clearing points above $70°$ C., preferably above $80°$ C., particularly preferably above $90°$ C., simultaneously birefringence values of $\leq 0.100$, preferably $\leq 0.095$, very particularly preferably $\leq 0.091$, and a low threshold voltage to be achieved, allowing excellent STN and MLC displays, in particular reflective MLC displays, to be achieved. In particular, the mixtures are characterized by low operating voltages. The TN thresholds are at about 1.5 V, preferably below 1.3 V, particularly preferably <1.0 V. Reflective MLC mixtures are particularly notable for TN thresholds <1.5 V.

It goes without saying that a suitable choice of the components of the mixtures according to the invention also allows higher clearing points (for example above 110° C.) to be achieved at the same time as lower dielectric anisotropy values and thus higher threshold voltages, or lower clearing points to be achieved at the same time as higher dielectric anisotropy values (for example >12) and thus lower threshold voltages (for example <1.5 V) while retaining the other advantageous properties. Likewise, mixtures of higher Δε and thus lower thresholds can be obtained at viscosities which are increased correspondingly little. The MLC displays according to the invention preferably operate at the first Gooch and Tarry transmission minimum [C. H. Gooch and H. A. Tarry, Electron. Lett. 10, 2–4, 1974; C. H. Gooch and H. A. Tarry, Appl. Phys., Vol. 8, 1575–1584, 1975], where, besides particularly favourable electro-optical properties, such as, for example, high steepness of the characteristic line and low angle dependence of the contrast (German Patent 30 22 818), a lower dielectric anisotropy is sufficient at the same threshold voltage as in an analogous display at the second minimum. Thus, significantly higher resistivities can be achieved using the mixtures according to the invention at the first minimum than in the case of mixtures comprising cyano compounds. A person skilled in the art can use simple routine methods to produce the birefringence necessary for a specified layer thickness of the MLC display by suitable choice of the individual components and their proportions by weight. The requirements of reflective MLC displays are described, for example, in Digest of Technical Papers, SID Symposium 1998.

The rotational viscosity of the mixtures according to the invention at 20° C. is preferably <200 mpa.s, particularly preferably <180 mPa.s. The nematic phase range is preferably at least 90°, in particular at least 100°. This range preferably extends at least from −20° to +80°.

Measurements of the capacity holding ratio, also known as the voltage holding ratio (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention comprising compounds of the formula I have an HR which is sufficient for MLC displays.

The media according to the invention preferably contain a plurality (preferably two, three or more) of compounds of the formula I, i.e. the proportion of these compounds is 5–50%, preferably 5–40%, particularly preferably in the range 5–35%.

The individual compounds of the formulae I to XV and their subformulae which can be used in the media according to the invention are either known or can be prepared analogously to the known compounds.

Preferred embodiments are indicated below:

Mixture comprising one or more compounds of the formulae Ia to Ik:

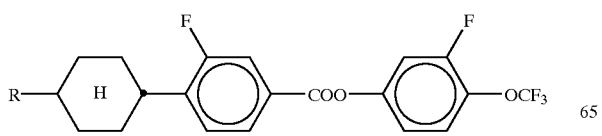

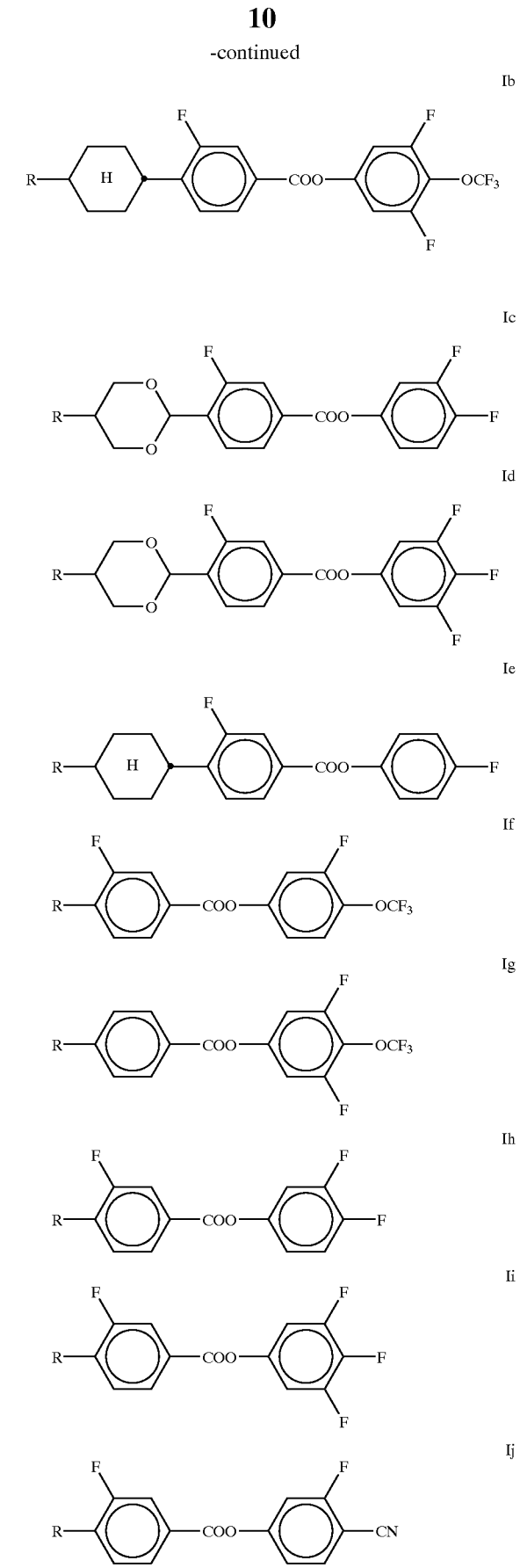

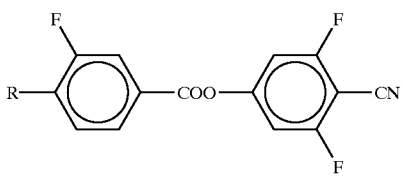

Ik

In the compounds of the formula I and of the sub-formulae Ia to Ik, R is preferably a straight-chain alkyl radical having 1-8 carbon atoms or an alkenyl radical having 2-8 carbon atoms. R is particularly preferably methyl, ethyl, n-propyl, n-pentyl, vinyl, 1E-propenyl and 3-butenyl.

The medium comprises one or more compounds of the formula Ia, Ib, Ic and/or Ik;

The medium additionally comprises one or more compounds selected from the group consisting of the general formulae II to VIII:

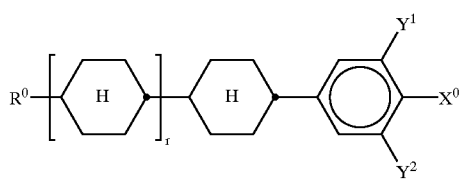

II

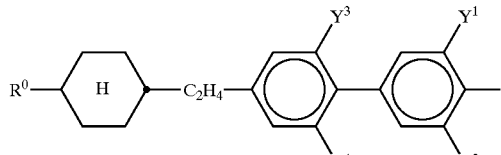

III

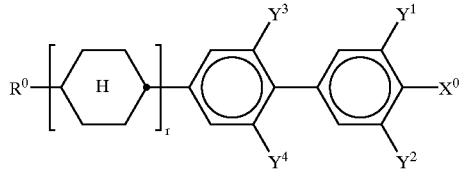

IV

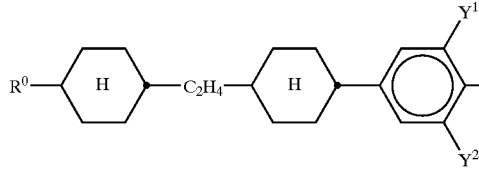

V

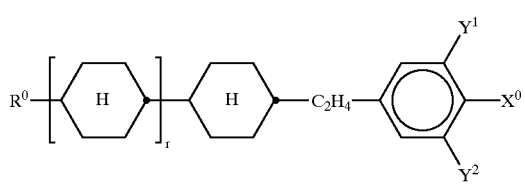

VI

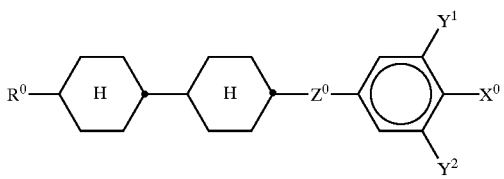

VII

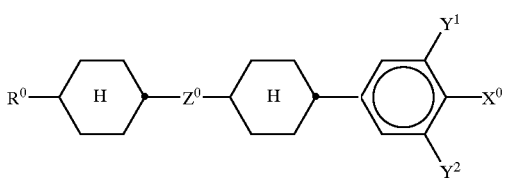

VIII in which the individual radicals have the following meanings:

$R^0$ is n-alkyl, oxaalkyl, fluoroalkyl or alkenyl, in each case having up to 9 carbon atoms;

$X^0$ is F, Cl, halogenated alkyl or alkoxy having 1 to 6 carbon atoms or halogenated alkenyl having 2 to 6 carbon atoms;

$Z^0$ is —$C_4H_8$—, $CF_2O$—, —$OCF_2$—, —$C_2F_4$— or —CH=CH—;

$Y^1$ to $Y^4$ are each, independently of one another, H or F;

r is 0 or 1.

The medium preferably comprises two, three, four or five compounds of the formula II;

The medium preferably comprises one or more compounds of the formulae IIa to IIh:

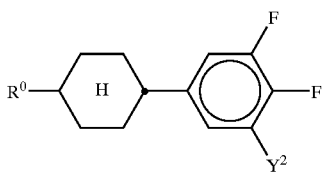

IIa

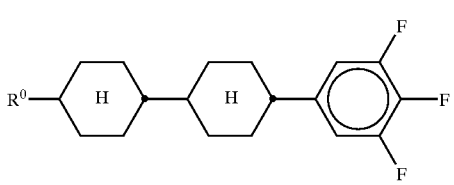

IIb

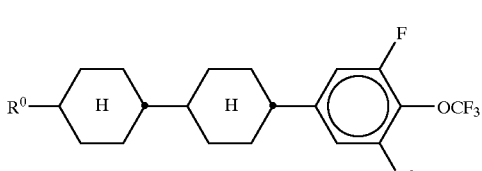

IIc

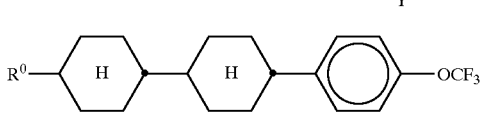

IId

IIe
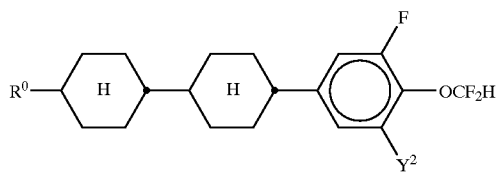
IIf
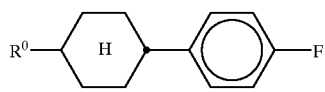
IIg
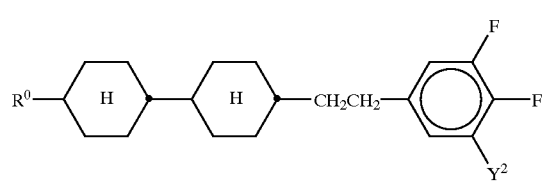
IIh
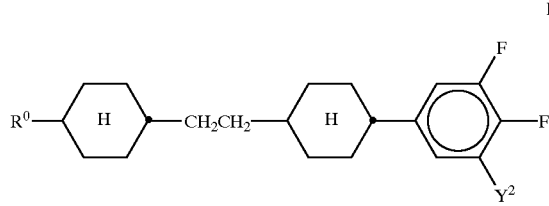
The compound of formula IV is preferably
IVa
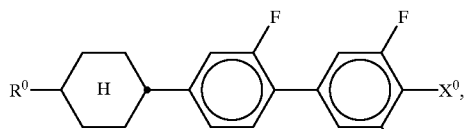
IVb
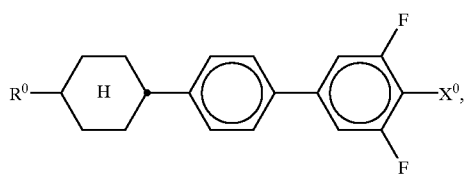
IVc
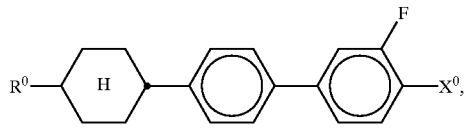
IVd
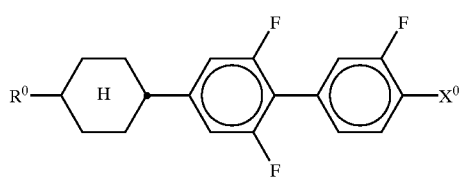
IVe
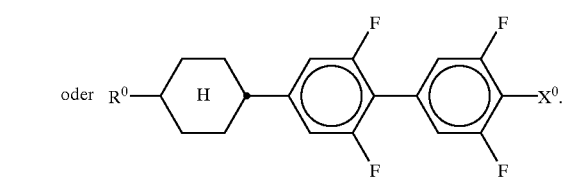
The medium additionally comprises one or more compounds selected from the group consisting of the general formulae IX to XV:
IX
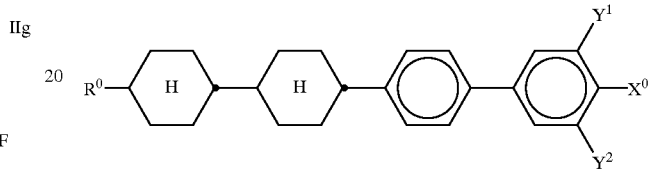
X
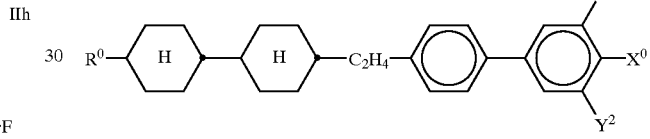
XI
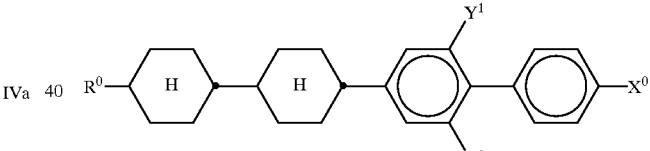
XII
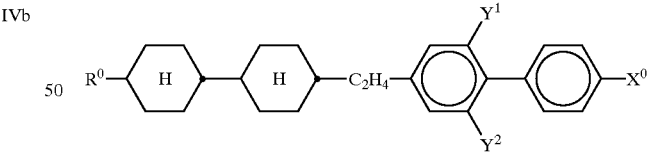
XIII
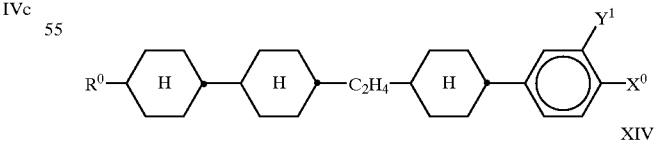
XIV
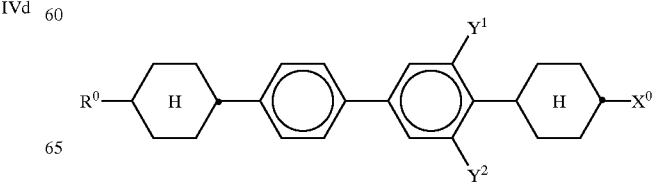

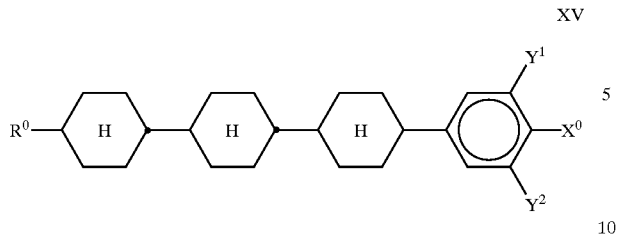

XV in which $R^0$, $X^0$, $Y^1$ and $y^2$ are each, independently of one another, as defined in claim 2. In the compounds of the formulae II to XV, $X^0$ is preferably F, Cl, $CF_3$, $OCF_3$, $OCHF_2$, in particular F and $OCF_3$, furthermore $OCHF_2$. $R^0$ is preferably alkyl, oxaalkyl, fluoroalkyl or alkenyl, in each case having up to 6 carbon atoms.

The medium additionally comprises one or more compounds of the formula

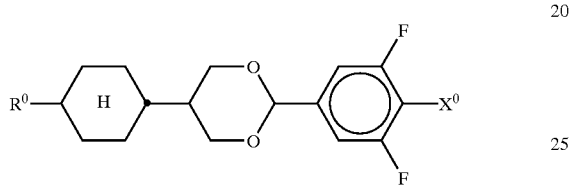

in which $R^0$ and $X^0$ are as defined above.

The medium additionally comprises one or more ester compounds of the formulae E1 to E5:

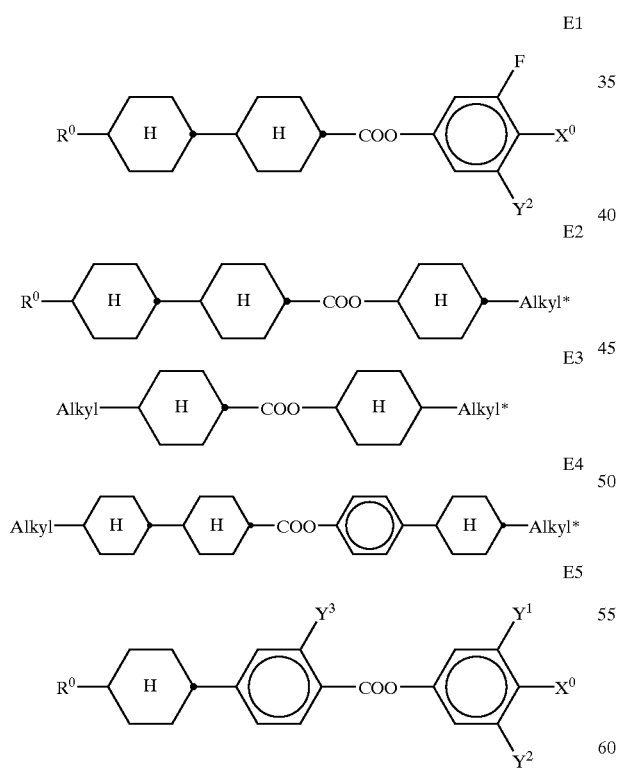

in which $R^0$, $X^0$, $y^1$, $y^2$ and $y^3$ are as defined above. Alkyl and alkyl* are each a straight-chain alkyl radical having 1 to 9 carbon atoms.

The medium additionally comprises one or more compounds of the formulae Xa to Xd:

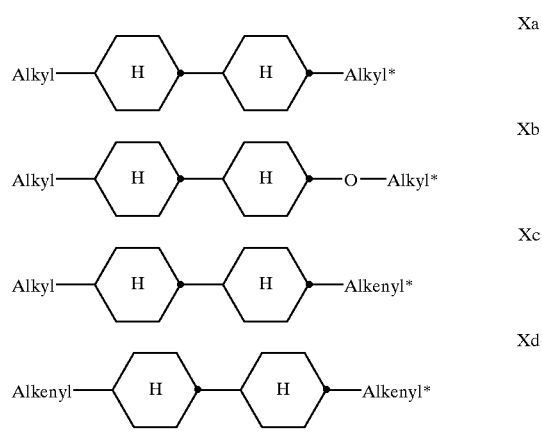

The medium additionally comprises one or more compounds of the formula E1a and/or E1b:

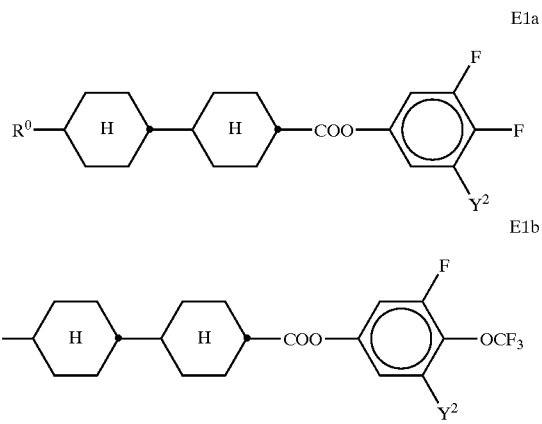

in which $R^0$ and $Y^2$ are as defined above.

The proportion of compounds of the formulae I to VIII together in the total mixture is at least 50% by weight;

The proportion of compounds of the formula I in the total mixture is from 5 to 50% by weight;

The proportion of compounds of the formulae II to VIII in the total mixture is from 20 to 80% by weight;

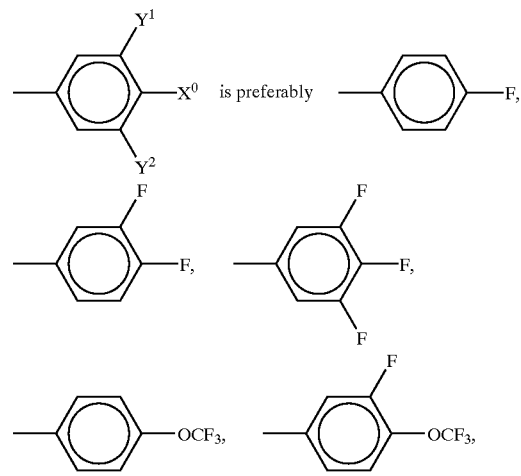

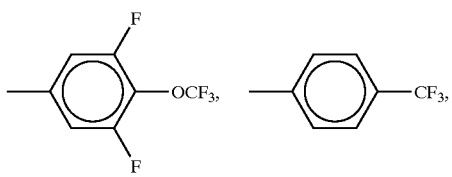

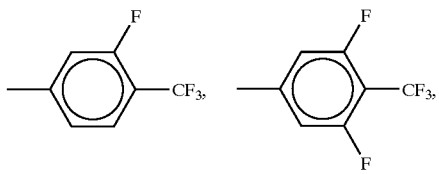

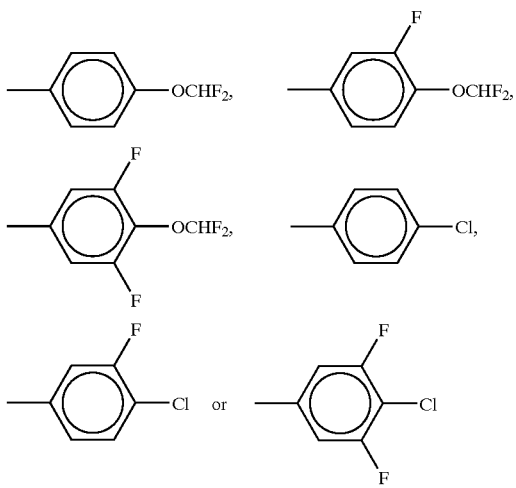

The medium comprises compounds of the formulae II, III, IV, V, VI, VII or VIII;

$R^0$ is preferably a straight-chain alkyl or alkenyl having 2 to 7 carbon atoms;

The medium essentially consists of compounds of the formulae I to VIII;

The medium comprises further compounds, preferably selected from the following group consisting of the general formulae XVI to XIX:

XVI

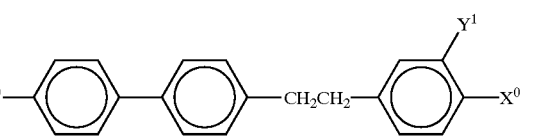

XVII

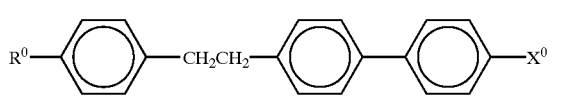

XVIII

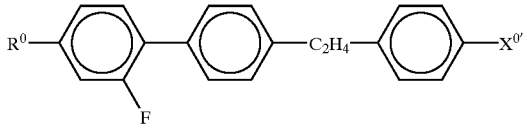

XIX $(X^{0'} = F$ oder $Cl)$ in which $R^0$ and $X^0$ are as defined above and the 1,4-phenylene rings can be substituted by CN, chlorine or fluorine. The 1,4-phenylene rings are preferably monosubstituted or polysubstituted by fluorine atoms.

The weight ratio I: (II+III+IV+V+VI+VII +VIII) is preferably from 1:10 to 10:1.

The medium essentially consists of compounds selected from the group consisting of the general formulae I to XV.

The proportion of compounds of the formulae Xa to Xd in the total mixture is 3–45% by weight, preferably 5–40% by weight, in particular 5–30% by weight.

The proportion of compounds of the formula E1 in the total mixture is 10–60% by weight, preferably 10–45% by weight, in particular 15–40% by weight.

The proportion of compounds of the formulae E2 and/or E3 in the total mixture is 1–30% by weight, preferably 3–20% by weight, in particular 3–15% by weight.

The proportion of compounds of the formula E4 is preferably ≦20% by weight, in particular ≦10% by weight.

It has been found that even a relatively small proportion of compounds of the formula I mixed with conventional liquid-crystal materials, but in particular with one or more compounds of the formula II, III, IV, V, VI, VII and/or VIII, leads to a decrease in the threshold voltage and to low birefringence values, where broad nematic phases with low smectic-nematic transition temperatures are simultaneously observed, which drastically improves the storage stability. Particularly preferred are mixtures which, in addition to one or more compounds of the formula I, comprise one or more compounds of the formula IV, in particular compounds of the formula IVa, where $X^0$ is F or $OCF_3$.

The compounds of the formulae I to VIII are colourless, stable and readily miscible with one another and with other liquid-crystalline materials.

The term "alkyl" or "alkyl*" encompasses straight-chain and branched alkyl groups having 1–7 carbon atoms, particularly the straight-chain groups methyl, ethyl, propyl, butyl, pentyl, hexyl and heptyl. Groups having 2–5 carbon atoms are generally preferred.

The term "alkenyl" or "alkenyl*" encompasses straight-chain and branched alkenyl groups having 2–7 carbon atoms, in particular the straight-chain groups. Particularly preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably encompasses straight-chain groups with terminal fluorine, i.e. fluoromethyl, 2-fluoroethyl, 3-fluoropropyl, 4-fluorobutyl, 5-fluoro-pentyl, 6-fluorohexyl and 7-fluoroheptyl. Other positions of fluorine are not precluded, however.

The term "oxaalkyl" preferably encompasses straight-chain radicals of the formula $C_nH_{2n+1}$—O—$(CH_2)_m$, where n and m are each, independently of one another, from 1 to 6. Preferably, n=1 and m is 1 to 6.

A suitable choice of the meanings of $R^0$ and $X_0$ allows the response times, the threshold voltage, the slope of the transmission characteristic lines etc. to be modified as desired. For example, 1E-alkenyl radicals, 3E-alkenyl radicals, 2E-alkenyloxy radicals and the like generally result in shorter response times, improved nematic tendencies and a higher ratio of the elastic constants $k_{33}$ (bend) and $k_{11}$ (splay) compared with alkyl or alkoxy radicals. 4-alkenyl radicals, 3-alkenyl radicals and the like generally result in lower threshold voltages and smaller values of $k_{33}/k_{11}$ compared with alkyl and alkoxy radicals.

The optimum weight ratio of compounds of the formulae I and II+III+IV+V+VI+VII+VIII largely depends on the desired properties, on the choice of the components of the formulae I, II, III, IV, V, VI, VII and/or VIII, and on the choice of any other components which may be present. Suitable weight ratios within the range given above can easily be determined from case to case.

The total amount of compounds of the formulae I to XV in the mixtures according to the invention is not critical. The mixtures can therefore comprise one or more further components in order to optimize various properties. However, the observed effect on the response times and the threshold voltage is usually greater the higher the total concentration of compounds of the formulae I to XV.

In a particularly preferred embodiment, the media according to the invention comprise compounds of the formulae II to VIII (preferably II, III and/or IV, especially IVa) in which $X^0$ is F, $OCF_3$, $OCHF_2$, F, OCH=$CF_2$, OCF=$CF_2$ or $OCF_2$—$CF_2H$. A favourable synergistic effect with the compounds of the formula I results in particularly advantageous properties. Mixtures comprising compounds of the formula I and of the formula IVa are particularly notable for their low threshold voltages.

The construction of the STN or MLC display according to the invention from polarizers, electrode base plates and surface-treated electrodes corresponds to the conventional construction for displays of this type. The term conventional construction is broadly drawn here and also covers all variations and modifications of the MLC display, in particular including matrix display elements based on poly-Si TFT or MIM and especially reflective displays.

A significant difference between the displays according to the invention and the conventional displays based on the twisted nematic cell consists, however, in the choice of the liquid-crystal parameters of the liquid-crystal layer.

The liquid-crystal mixtures which can be used in accordance with the invention are prepared in a manner conventional per se. In general, the desired amount of the components used in a lesser amount is dissolved in the components making up the principal constituent, expediently at elevated temperature. It is also possible to mix solutions of the components in an organic solvent, for example in acetone, chloroform or methanol, and to remove the solvent again after thorough mixing, for example by distillation. It is also possible to prepare the mixtures in other conventional manners, for example by using pre-mixtures, for example homologue mixtures, or using so-called "multi-bottle" systems.

The dielectrics may also comprise further additives known to the person skilled in the art and described in the literature. For example, 0–15%, preferably 0–10%, of pleochroic dyes and/or chiral dopants can be added. The additives are each employed in concentrations of from 0.01 to 6%, preferably from 0.1 to 3%. However, the concentration data for the other constituents of the liquid-crystal mixtures, i.e. of the liquid-crystalline or mesogenic compounds, are given without taking into account the concentration of these additives.

C denotes a crystalline phase, S a smectic phase, $S_c$ a smectic C phase, N a nematic phase and I the isotropic phase.

The entire disclosure of all applications, patents and publications, cited above, and of corresponding German application No. DE 19954906.0, filed Nov. 16, 1999, is hereby incorporated by reference.

In the present application and in the following examples, the structures of the liquid crystal compounds are specified by acronyms, which can be transformed into chemical formulae according to the following Tables A and B. All radicals $C_nH_{2n+1}$ and $C_mH_{2m+1}$ are straight-chain alkyl radicals having n or m C atoms. n and m are integers, preferably 0, 1, 2, 3, 4, 5, 6, 7, 8, 9, 10, 11 or 12, where n=m or n≠m. The coding according to Table B is self-evident. Table A specifies the acronym for the parent body only. In individual cases, the acronym for the parent body is followed, separated therefrom by a hyphen, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| $nCF_3$ | $C_nH_{2n+1}$ | $CF_3$ | H | H |
| $nOCF_3$ | $C_nH_{2n+1}$ | $OCF_3$ | H | H |
| $nOCF_2$ | $C_nH_{2n+1}$ | $OCHF_2$ | H | H |
| nS | $C_nH_{2n+1}$ | NCS | H | H |
| rVsN | $C_rH_{2r+1}$—CH=CH—$C_sH_{2s}$— | CN | H | H |
| V-T | $CH_2$=CH | $CF_3$ | H | H |
| V2-T | $CH_2$—CH—$C_2H_4$ | $CF_3$ | H | H |
| 1V-OT | $CH_3$—CH=CH | $OCF_3$ | H | H |
| rEsN | $C_rH_{2r+1}$—O—$C_2H_{2s}$— | CN | H | H |
| nAm | $C_nH_{2n+1}$ | $COOC_mH_{2m+1}$ | H | H |
| $nOCCF_2.F.F$ | $C_nH_{2n+1}$ | $OCH_2CF_2H$ | F | F |

Preferred mixture components are shown in Tables A and B.
TABLE A
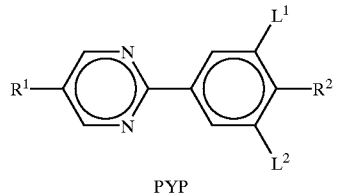
PYP
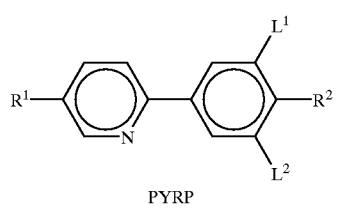
PYRP
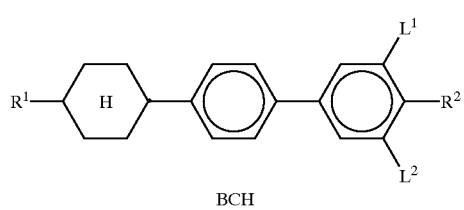
BCH
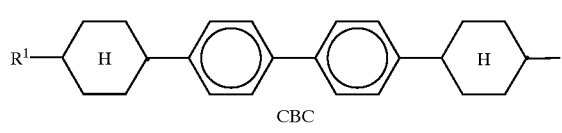
CBC
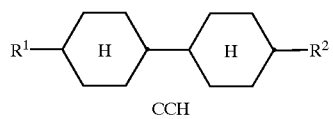
CCH
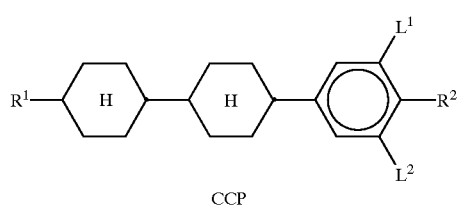
CCP
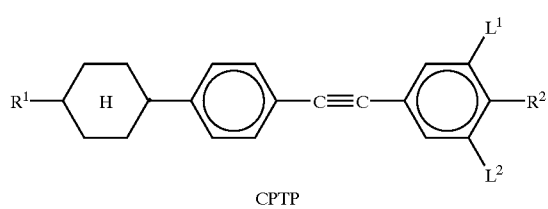
CPTP
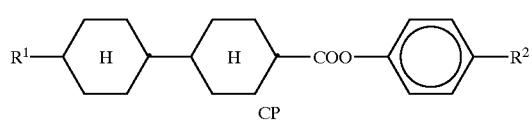
CP
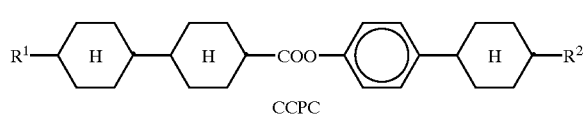
CCPC
TABLE A-continued
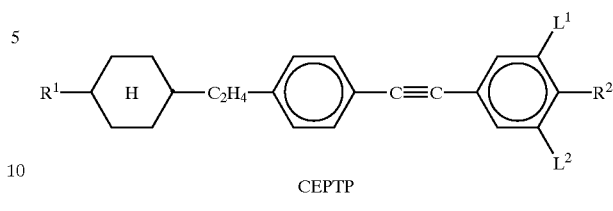
CEPTP
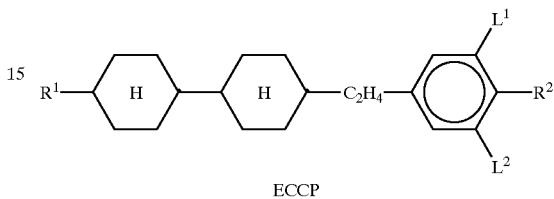
ECCP
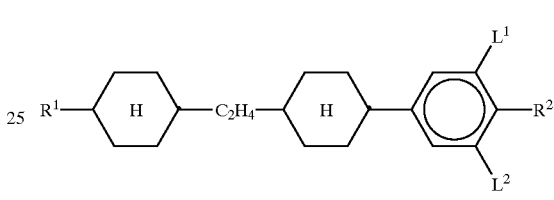
CECP
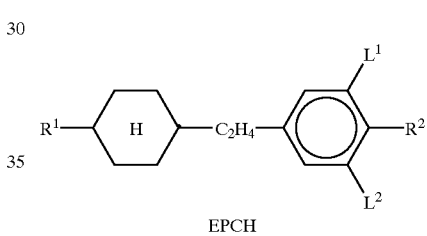
EPCH
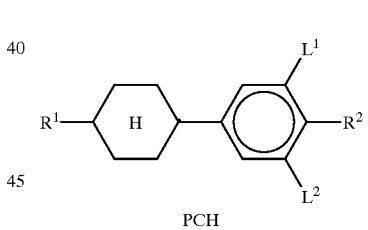
PCH
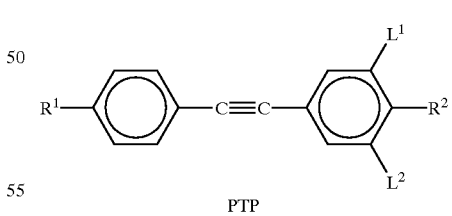
PTP
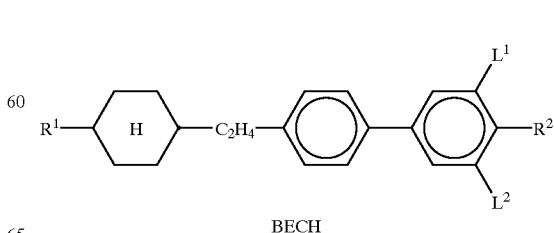
BECH TABLE A-continued
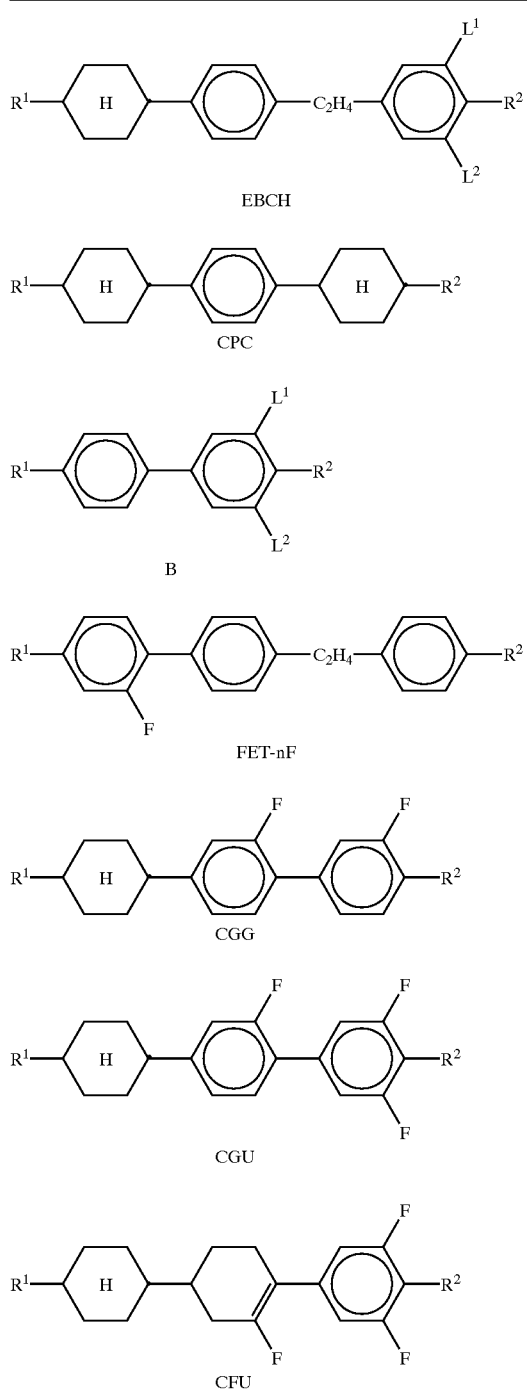
TABLE B
TABLE B-continued
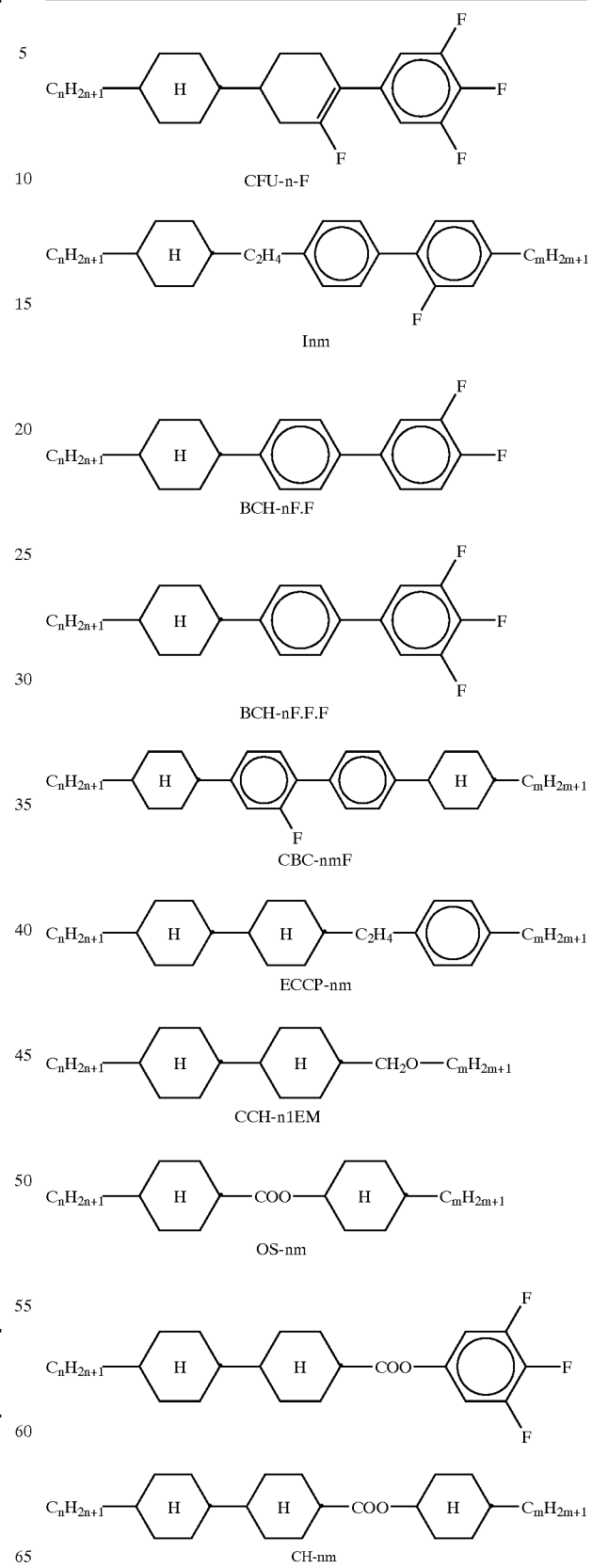
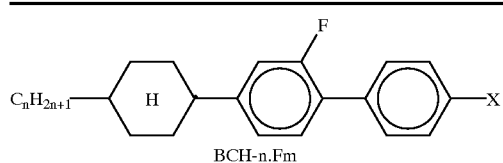

TABLE B-continued
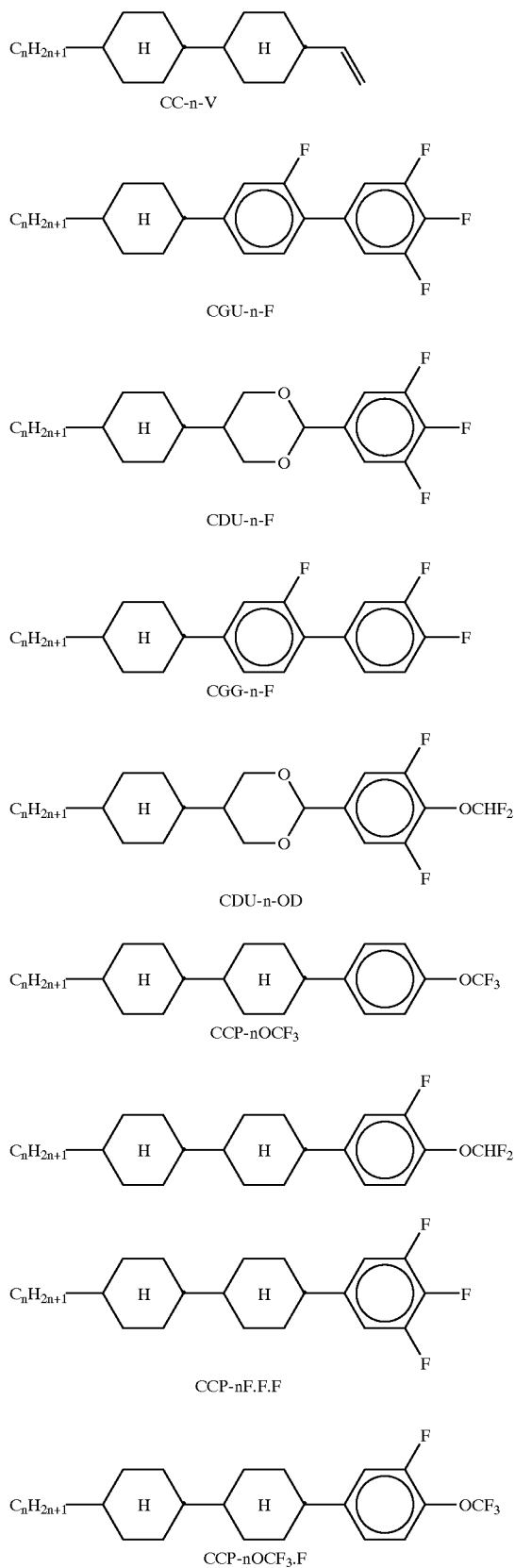
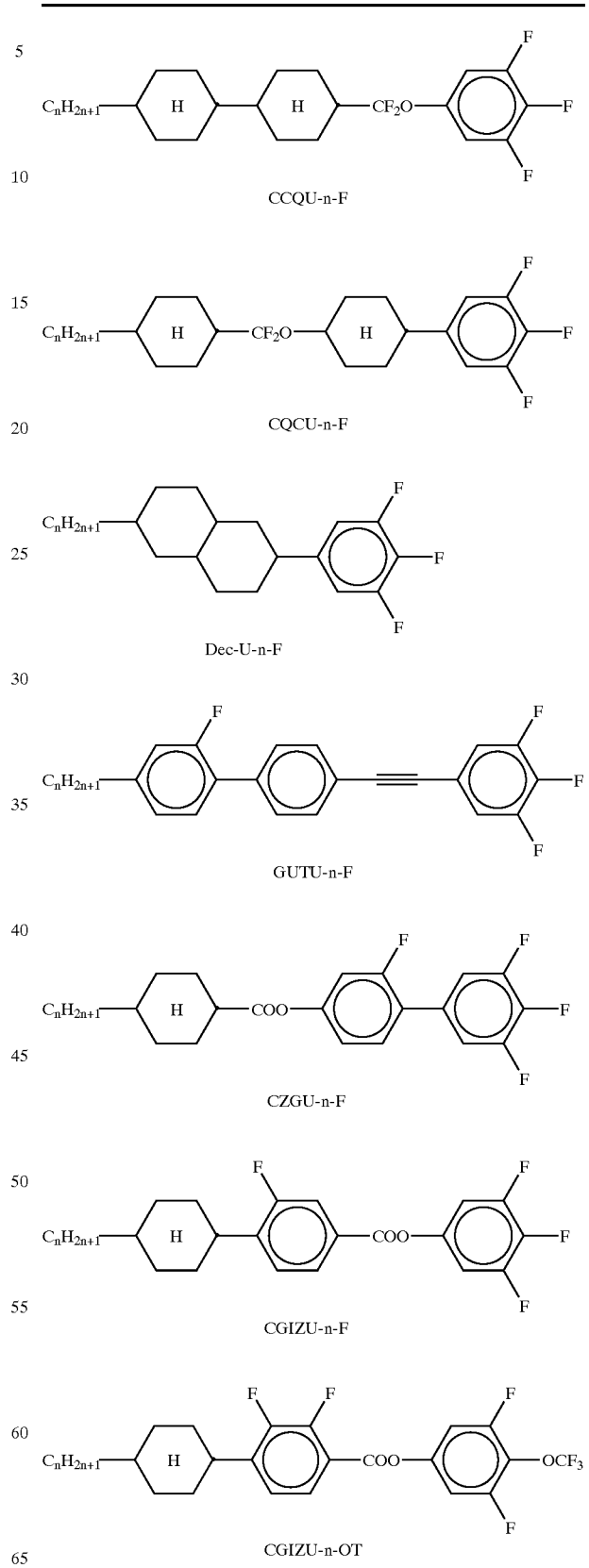

TABLE B-continued

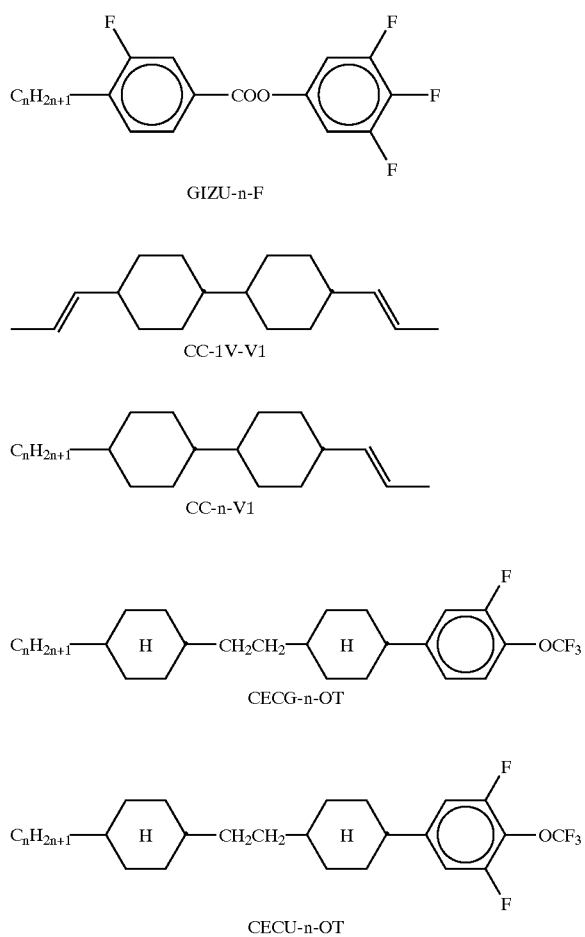

TABLE C

Table C lists possible dopants which are usually added to the mixtures according to the invention.

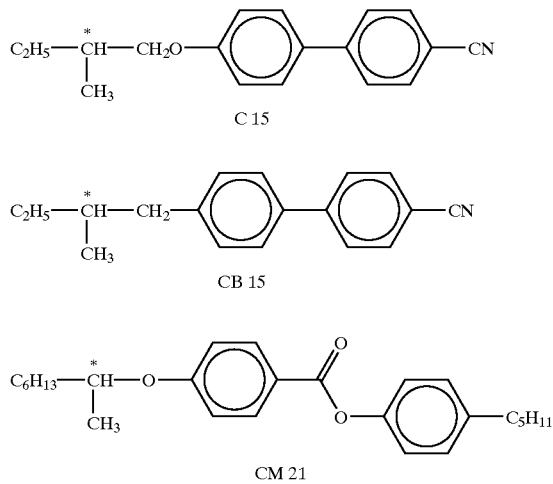

TABLE C-continued

Table C lists possible dopants which are usually added to the mixtures according to the invention.

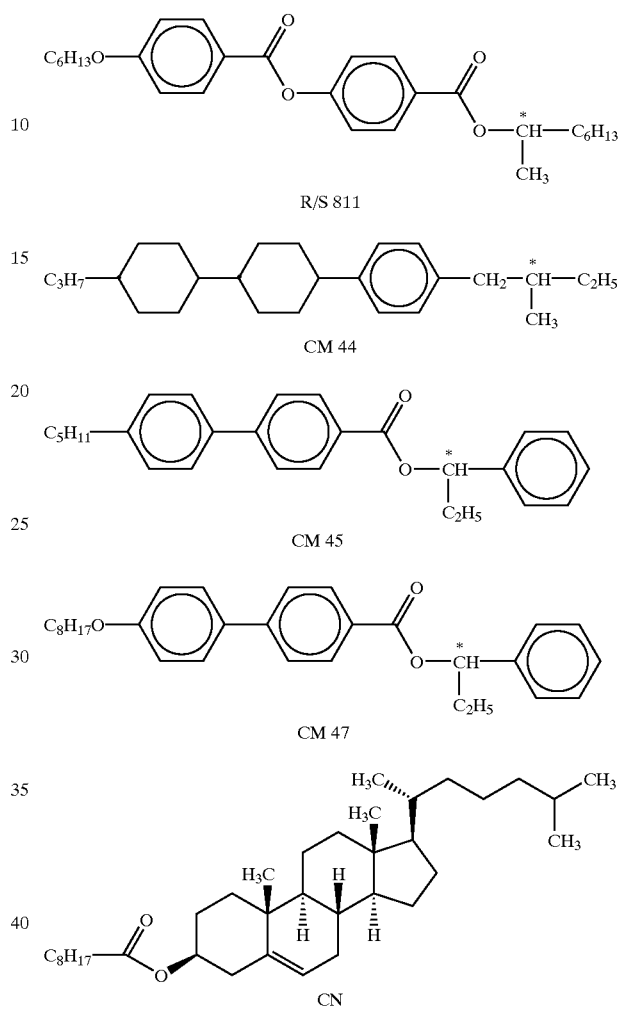

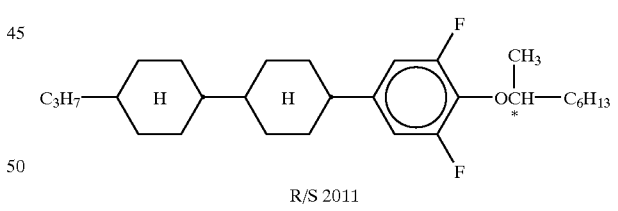

Particular preference is given to mixtures according to the invention which, in addition to one or more compounds of the formula I, comprise two, three or more compounds selected from Table B.

The following examples are intended to illustrate the invention without limiting it. Hereinbefore and hereinafter, percentages are given in per cent by weight. All temperatures are specified in degrees Celsius. m.p. denotes melting point, cl.p.=clearing point. Furthermore, C=crystalline state, N=nematic phase, S=smectic phase and I=isotropic phase. The data between these symbols represent the transition temperatures. The optical anisotropy (589 nm, 20° C.), and the flow viscosity $v_{20}$ (mm$^2$/sec) and the rotational viscosity $\gamma_1$ (mPa·s) were each determined at 20° C. $v_{10}$ denotes the voltage for 10% transmission (viewing direction perpendicular to the substrate surface). $t_{on}$ denotes the on time and $t_{off}$ the off time at an operating voltage corresponding to twice the value of $V_{10}$. $\Delta n$ denotes the optical anisotropy and $n_0$ the refractive index. $\Delta\epsilon$ denotes the dielectric anisotropy ($\Delta\epsilon=\epsilon_{II}-\epsilon_{\perp}$, where $\epsilon_{II}$ refers to the dielectric constant parallel to the longitudinal axes of the molecule and $\epsilon_{\perp}$ is the dielectric constant perpendicular thereto). The electro-optical data were measured in a TN cell in the 1st minimum (i.e. at a d·$\Delta n$ value of 0.5) at 20° C., unless expressly stated otherwise. The optical data were measured at 20° C., unless expressly stated otherwise.

EXAMPLES

Example 1

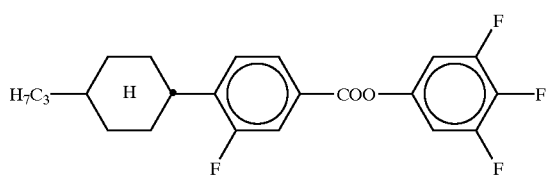

Step 1.1

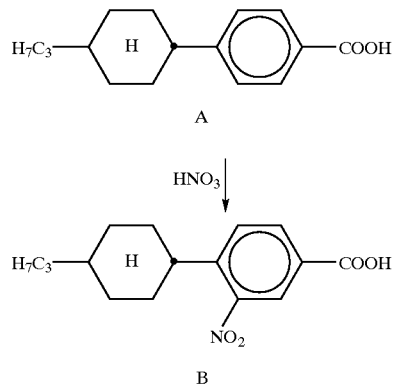

90 ml of concentrated sulfuric acid are added dropwise to an initial charge of 62.2 ml of nitric acid at about 0° C. (nitrating acid). The nitrating acid is added dropwise at about 0° C. to a suspension of 1 mol of A in 1.1 l of dichloromethane. The mixture is stirred for 2 h at about 0° C. and then admixed with ice-water. After extracting with dichloromethane and then with water, the crystals are recrystallized from toluene.

Step 1.2

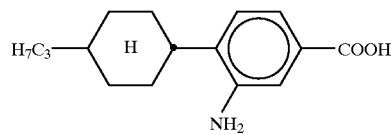

0.5 mol of B are hydrogenated in 1.3 l of abs. THF in the presence of 20.7 g Pd-C (5%) catalyst.

After hydrogenation is complete, the catalyst is filtered off and the solvent is removed under reduced pressure. The product is subjected to customary work-up.

Step 1.3

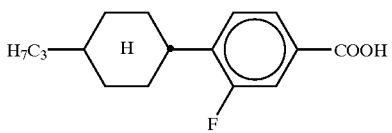

An initial charge of 250 ml of hydrogen fluoride (65% strength solution in pyridine) is cooled to 5° C. After addition of 0.175 mol of C, stirring is continued for another 1.5 h. At 10° C., 0.175 mol sodium nitrite is added portion-wise to the reaction solution at 5–10° C. The reaction solution is then slowly warmed to 60° C., stirred at this temperature for 0.5 h and then stirred at room temperature overnight. After addition of ice, the mixture is subjected to customary work-up. The product is recrystallized from ethyl acetate.

Step 1.4

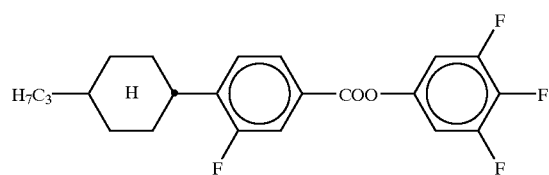

A solution of 0.031 mol of N,N'-dicyclohexylcarbo-diimide in 15 ml of dichloromethane is added dropwise at 10° C. to a suspension of 0.025 mol of D, 0.026 mol of 3,4,5-trifluorophenol and 0.001 mol of 4-(dimethyl-amino)-pyridine in 55 ml of dichloromethane, produced at room temperature.

The reaction solution is stirred at room temperature overnight, admixed with 0.026 mol of oxalic acid dihydrate and stirred for another 10 minutes. Finally, the mixture is subjected to customary work-up. The product is recrystallized from n-hexane. C 85 N (67.2) I; $\Delta\epsilon$=15.18; $\Delta n$=0.13.

The following compounds of the formula

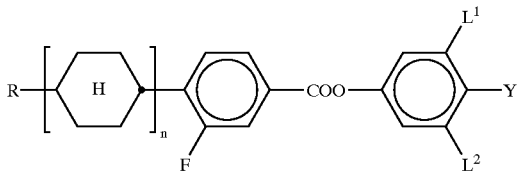

are prepared in a similar manner:

| R | n | Y | $L^1$ | $L^2$ |
|---|---|---|---|---|
| $CH_3$ | 1 | F | H | H |
| $CH_3$ | 1 | F | H | F |
| $CH_3$ | 1 | F | F | F |
| $C_2H_5$ | 1 | F | H | H |
| $C_2H_5$ | 1 | F | H | F |
| $C_2H_5$ | 1 | F | F | F C 98.1; $\Delta\epsilon$ = 14.67; $\Delta n$ = 0.12 |

| R | n | Y | L¹ | L² |
|---|---|---|---|---|
| n-C$_3$H$_7$ | 1 | F | H | H |
| n-C$_3$H$_7$ | 1 | F | H | F |
| n-C$_4$H$_9$ | 1 | F | H | H |
| n-C$_4$H$_9$ | 1 | F | H | F |
| n-C$_4$H$_9$ | 1 | F | F | F |
| n-C$_5$H$_{11}$ | 1 | F | H | H |
| n-C$_5$H$_{11}$ | 1 | F | H | F C58 N 106, I; Δε = 8.92; Δn = 0.12 |
| n-C$_5$H$_{11}$ | 1 | F | F | F C71 N 81.6; I; Δε = 14.61; Δn = 0.12 |
| n-C$_6$H$_{13}$ | 1 | F | H | H |
| n-C$_6$H$_{13}$ | 1 | F | H | F |
| n-C$_6$H$_{13}$ | 1 | F | F | F |
| CH$_2$=CH | 1 | F | H | H |
| CH$_2$=CH | 1 | F | H | F |
| CH$_2$=CH | 1 | F | F | F |
| CH$_3$CH=CH | 1 | F | H | H |
| CH$_3$CH=CH | 1 | F | H | F |
| CH$_3$CH=CH | 1 | F | F | F |
| CH$_2$=CHC$_2$H$_4$ | 1 | F | H | H |
| CH$_2$=CHC$_2$H$_4$ | 1 | F | H | F |
| CH$_2$=CHC$_2$H$_4$ | 1 | F | F | F |
| CH$_3$CH=CHC$_2$H$_4$ | 1 | F | H | H |
| CH$_3$CH=CHC$_2$H$_4$ | 1 | F | H | F |
| CH$_3$CH=CHC$_2$H$_4$ | 1 | F | F | F |
| CH$_3$O | 1 | F | H | H |
| CH$_3$O | 1 | F | H | F |
| CH$_3$O | 1 | F | F | F |
| CH$_3$ | 1 | Cl | H | H |
| CH$_3$ | 1 | Cl | H | F |
| CH$_3$ | 1 | Cl | F | F |
| C$_2$H$_5$ | 1 | Cl | H | H |
| C$_2$H$_5$ | 1 | Cl | H | F |
| C$_2$H$_5$ | 1 | Cl | F | F |
| n-C$_3$H$_7$ | 1 | Cl | H | H |
| n-C$_3$H$_7$ | 1 | Cl | H | F |
| n-C$_3$H$_7$ | 1 | Cl | F | F |
| n-C$_4$H$_9$ | 1 | Cl | H | H |
| n-C$_4$H$_9$ | 1 | Cl | H | F |
| n-C$_4$H$_9$ | 1 | Cl | F | F |
| n-C$_5$H$_{11}$ | 1 | Cl | H | H |
| n-C$_5$H$_{11}$ | 1 | Cl | H | F |
| n-C$_5$H$_{11}$ | 1 | Cl | F | F |
| n-C$_6$H$_{13}$ | 1 | Cl | H | H |
| n-C$_6$H$_{13}$ | 1 | Cl | H | F |
| n-C$_6$H$_{13}$ | 1 | Cl | F | F |
| CH$_2$=CH | 1 | Cl | H | H |
| CH$_2$=CH | 1 | Cl | H | F |
| CH$_2$=CH | 1 | Cl | F | F |
| CH$_3$CH=CH | 1 | Cl | H | H |
| CH$_3$CH=CH | 1 | Cl | H | F |
| CH$_3$CH=CH | 1 | Cl | F | F |
| CH$_2$=CHC$_2$H$_4$ | 1 | Cl | H | H |
| CH$_2$=CHC$_2$H$_4$ | 1 | Cl | H | F |
| CH$_2$=CHC$_2$H$_4$ | 1 | Cl | F | F |
| CH$_3$CH=CHC$_2$H$_4$ | 1 | Cl | H | H |
| CH$_3$CH=CHC$_2$H$_4$ | 1 | Cl | H | F |
| CH$_3$CH=CHC$_2$H$_4$ | 1 | Cl | F | F |
| CH$_3$O | 1 | Cl | H | H |
| CH$_3$O | 1 | Cl | H | F |
| CH$_3$O | 1 | Cl | F | F |
| CH$_3$ | 1 | OCF$_3$ | H | H |
| CH$_3$ | 1 | OCF$_3$ | H | F |
| CH$_3$ | 1 | OCF$_3$ | F | F |
| C$_2$H$_5$ | 1 | OCF$_3$ | H | H C58 S$_A$ 88 N 115 I; Δε = 8.57; Δn = 0.13 |
| C$_2$H$_5$ | 1 | OCF$_3$ | H | F |
| C$_2$H$_5$ | 1 | OCF$_3$ | F | F |
| n-C$_3$H$_7$ | 1 | OCF$_3$ | H | H C75 S$_A$ 80 N 143 I; Δε = 8.66; Δn = 0.13 |
| n-C$_3$H$_7$ | 1 | OCF$_3$ | H | F |
| n-C$_3$H$_7$ | 1 | OCF$_3$ | F | F |
| n-C$_4$H$_9$ | 1 | OCF$_3$ | H | H |
| n-C$_4$H$_9$ | 1 | OCF$_3$ | H | F |
| n-C$_4$H$_9$ | 1 | OCF$_3$ | F | F |
| n-C$_5$H$_{11}$ | 1 | OCF$_3$ | H | H C84 S$_A$ 86 N 140.8 I; Δε = 7.91; Δn = 0.12 |
| n-C$_5$H$_{11}$ | 1 | OCF$_3$ | H | F |
| n-C$_5$H$_{11}$ | 1 | OCF$_3$ | F | F |
| n-C$_6$H$_{13}$ | 1 | OCF$_3$ | H | H |
| n-C$_6$H$_{13}$ | 1 | OCF$_3$ | H | F |
| n-C$_6$H$_{13}$ | 1 | OCF$_3$ | F | F |
| CH$_2$=CH | 1 | OCF$_3$ | H | H |
| CH$_2$=CH | 1 | OCF$_3$ | H | F |
| CH$_2$=CH | 1 | OCF$_3$ | F | F |
| CH$_3$CH=CH | 1 | OCF$_3$ | H | H |
| CH$_3$CH=CH | 1 | OCF$_3$ | H | F |
| CH$_3$CH=CH | 1 | OCF$_3$ | F | F |
| CH$_2$=CHC$_2$H$_4$ | 1 | OCF$_3$ | H | H |
| CH$_2$=CHC$_2$H$_4$ | 1 | OCF$_3$ | H | F |
| CH$_2$=CHC$_2$H$_4$ | 1 | OCF$_3$ | F | F |
| CH$_3$CH=CHC$_2$H$_4$ | 1 | OCF$_3$ | H | H |
| CH$_3$CH=CHC$_2$H$_4$ | 1 | OCF$_3$ | H | F |
| CH$_3$CH=CHC$_2$H$_4$ | 1 | OCF$_3$ | F | F |
| CH$_3$O | 1 | OCF$_3$ | H | H |
| CH$_3$O | 1 | OCF$_3$ | H | F |
| CH$_3$O | 1 | OCF$_3$ | F | F |
| CH$_3$ | 1 | OCHF$_2$ | H | H |
| CH$_3$ | 1 | OCHF$_2$ | H | F |
| CH$_3$ | 1 | OCHF$_2$ | F | F |
| C$_2$H$_5$ | 1 | OCHF$_2$ | H | H |
| C$_2$H$_5$ | 1 | OCHF$_2$ | H | F |
| C$_2$H$_5$ | 1 | OCHF$_2$ | F | F |
| n-C$_3$H$_7$ | 1 | OCHF$_2$ | H | H |
| n-C$_3$H$_7$ | 1 | OCHF$_2$ | H | F |
| n-C$_3$H$_7$ | 1 | OCHF$_2$ | F | F |
| n-C$_4$H$_9$ | 1 | OCHF$_2$ | H | H |
| n-C$_4$H$_9$ | 1 | OCHF$_2$ | H | F |
| n-C$_4$H$_9$ | 1 | OCHF$_2$ | F | F |
| n-C$_5$H$_{11}$ | 1 | OCHF$_2$ | H | H |
| n-C$_5$H$_{11}$ | 1 | OCHF$_2$ | H | F |
| n-C$_5$H$_{11}$ | 1 | OCHF$_2$ | F | F |
| n-C$_6$H$_{13}$ | 1 | OCHF$_2$ | H | H |
| n-C$_6$H$_{13}$ | 1 | OCHF$_2$ | H | F |
| n-C$_6$H$_{13}$ | 1 | OCHF$_2$ | F | F |
| CH$_2$=CH | 1 | OCHF$_2$ | H | H |
| CH$_2$=CH | 1 | OCHF$_2$ | H | F |
| CH$_2$=CH | 1 | OCHF$_2$ | F | F |
| CH$_3$CH=CH | 1 | OCHF$_2$ | H | H |
| CH$_3$CH=CH | 1 | OCHF$_2$ | H | F |
| CH$_3$CH=CH | 1 | OCHF$_2$ | F | F |
| CH$_2$=CHC$_2$H$_4$ | 1 | OCHF$_2$ | H | H |
| CH$_2$=CHC$_2$H$_4$ | 1 | OCHF$_2$ | H | F |
| CH$_2$=CHC$_2$H$_4$ | 1 | OCHF$_2$ | F | F |
| CH$_3$CH=CHC$_2$H$_4$ | 1 | OCHF$_2$ | H | H |
| CH$_3$CH=CHC$_2$H$_4$ | 1 | OCHF$_2$ | H | F |
| CH$_3$CH=CHC$_2$H$_4$ | 1 | OCHF$_2$ | F | F |
| CH$_3$O | 1 | OCHF$_2$ | H | H |
| CH$_3$O | 1 | OCHF$_2$ | H | F |
| CH$_3$O | 1 | OCHF$_2$ | F | F |
| CH$_3$ | 1 | CN | H | H |
| CH$_3$ | 1 | CN | H | F |
| CH$_3$ | 1 | CN | F | F |
| C$_2$H$_5$ | 1 | CN | H | H |
| C$_2$H$_5$ | 1 | CN | H | F |
| C$_2$H$_5$ | 1 | CN | F | F |
| n-C$_3$H$_7$ | 1 | CN | H | H |
| n-C$_3$H$_7$ | 1 | CN | H | F |
| n-C$_3$H$_7$ | 1 | CN | F | F |
| n-C$_4$H$_9$ | 1 | CN | H | H |
| n-C$_4$H$_9$ | 1 | CN | H | F |
| n-C$_4$H$_9$ | 1 | CN | F | F |
| n-C$_5$H$_{11}$ | 1 | CN | H | H |
| n-C$_5$H$_{11}$ | 1 | CN | H | F |
| n-C$_5$H$_{11}$ | 1 | CN | F | F |
| n-C$_6$H$_{13}$ | 1 | CN | H | H |
| n-C$_6$H$_{13}$ | 1 | CN | H | F |
| n-C$_6$H$_{13}$ | 1 | CN | F | F |

-continued

| R | n | Y | L¹ | L² |
|---|---|---|----|----|
| CH$_2$=CH | 1 | CN | H | H |
| CH$_2$=CH | 1 | CN | H | F |
| CH$_2$=CH | 1 | CN | F | F |
| CH$_3$CH=CH | 1 | CN | H | H |
| CH$_3$CH=CH | 1 | CN | H | F |
| CH$_3$CH=CH | 1 | CN | F | F |
| CH$_2$=CHC$_2$H$_4$ | 1 | CN | H | H |
| CH$_2$=CHC$_2$H$_4$ | 1 | CN | H | F |
| CH$_2$=CHC$_2$H$_4$ | 1 | CN | F | F |
| CH$_3$CH=CHC$_2$H$_4$ | 1 | CN | H | H |
| CH$_3$CH=CHC$_2$H$_4$ | 1 | CN | H | F |
| CH$_3$CH=CHC$_2$H$_4$ | 1 | CN | F | F |
| CH$_3$O | 1 | CN | H | H |
| CH$_3$O | 1 | CN | H | F |
| CH$_3$O | 1 | CN | F | F |
| CH$_3$ | 0 | F | H | H |
| CH$_3$ | 0 | F | H | F |
| CH$_3$ | 0 | F | F | F |
| C$_2$H$_5$ | 0 | F | H | H |
| C$_2$H$_5$ | 0 | F | H | F |
| C$_2$H$_5$ | 0 | F | F | F |
| n-C$_3$H$_7$ | 0 | F | H | H |
| n-C$_3$H$_7$ | 0 | F | H | F |
| n-C$_3$H$_7$ | 0 | F | F | F |
| n-C$_4$H$_9$ | 0 | F | H | H |
| n-C$_4$H$_9$ | 0 | F | H | F |
| n-C$_4$H$_9$ | 0 | F | F | F |
| n-C$_5$H$_{11}$ | 0 | F | H | H |
| n-C$_5$H$_{11}$ | 0 | F | H | F |
| n-C$_5$H$_{11}$ | 0 | F | F | F $\Delta\epsilon$ = 31.0; $\Delta n$ = 0.165 |
| n-C$_6$H$_{13}$ | 0 | F | H | H |
| n-C$_6$H$_{13}$ | 0 | F | H | F |
| n-C$_6$H$_{13}$ | 0 | F | F | F |
| CH$_2$=CH | 0 | F | H | H |
| CH$_2$=CH | 0 | F | H | F |
| CH$_2$=CH | 0 | F | F | F |
| CH$_3$CH=CH | 0 | F | H | H |
| CH$_3$CH=CH | 0 | F | H | F |
| CH$_3$CH=CH | 0 | F | F | F |
| CH$_2$=CHC$_2$H$_4$ | 0 | F | H | H |
| CH$_2$=CHC$_2$H$_4$ | 0 | F | H | F |
| CH$_2$=CHC$_2$H$_4$ | 0 | F | F | F |
| CH$_3$CH=CHC$_2$H$_4$ | 0 | F | H | H |
| CH$_3$CH=CHC$_2$H$_4$ | 0 | F | H | F |
| CH$_3$CH=CHC$_2$H$_4$ | 0 | F | F | F |
| CH$_3$O | 0 | F | H | H |
| CH$_3$O | 0 | F | H | F |
| CH$_3$O | 0 | F | F | F |
| CH$_3$ | 0 | Cl | H | H |
| CH$_3$ | 0 | Cl | H | F |
| CH$_3$ | 0 | Cl | F | F |
| C$_2$H$_5$ | 0 | Cl | H | H |
| C$_2$H$_5$ | 0 | Cl | H | F |
| C$_2$H$_5$ | 0 | Cl | F | F |
| n-C$_3$H$_7$ | 0 | Cl | H | H |
| n-C$_3$H$_7$ | 0 | Cl | H | F |
| n-C$_3$H$_7$ | 0 | Cl | F | F |
| n-C$_4$H$_9$ | 0 | Cl | H | H |
| n-C$_4$H$_9$ | 0 | Cl | H | F |
| n-C$_4$H$_9$ | 0 | Cl | F | F |
| n-C$_5$H$_{11}$ | 0 | Cl | H | H |
| n-C$_5$H$_{11}$ | 0 | Cl | H | F |
| n-C$_5$H$_{11}$ | 0 | Cl | F | F |
| n-C$_6$H$_{13}$ | 0 | Cl | H | H |
| n-C$_6$H$_{13}$ | 0 | Cl | H | F |
| n-C$_6$H$_{13}$ | 0 | Cl | F | F |
| CH$_2$=CH | 0 | Cl | H | H |
| CH$_2$=CH | 0 | Cl | H | F |
| CH$_2$=CH | 0 | Cl | F | F |
| CH$_3$CH=CH | 0 | Cl | H | H |
| CH$_3$CH=CH | 0 | Cl | H | F |
| CH$_3$CH=CH | 0 | Cl | F | F |
| CH$_2$=CHC$_2$H$_4$ | 0 | Cl | H | H |
| CH$_2$=CHC$_2$H$_4$ | 0 | C | H | F |
| CH$_2$=CHC$_2$H$_4$ | 0 | Cl | F | F |
| CH$_3$CH=CHC$_2$H$_4$ | 0 | Cl | H | H |
| CH$_3$CH=CHC$_2$H$_4$ | 0 | Cl | H | F |
| CH$_3$CH=CHC$_2$H$_4$ | 0 | Cl | F | F |
| CH$_3$O | 0 | Cl | H | H |
| CH$_3$O | 0 | Cl | H | F |
| CH$_3$O | 0 | Cl | F | F |
| CH$_3$ | 0 | OCF$_3$ | H | H |
| CH$_3$ | 0 | OCF$_3$ | H | F |
| CH$_3$ | 0 | OCF$_3$ | F | F |
| C$_2$H$_5$ | 0 | OCF$_3$ | H | H |
| C$_2$H$_5$ | 0 | OCF$_3$ | H | F |
| C$_2$H$_5$ | 0 | OCF$_3$ | F | F |
| n-C$_3$H$_7$ | 0 | OCF$_3$ | H | H |
| n-C$_3$H$_7$ | 0 | OCF$_3$ | H | F |
| n-C$_3$H$_7$ | 0 | OCF$_3$ | F | F |
| n-C$_4$H$_9$ | 0 | OCF$_3$ | H | H |
| n-C$_4$H$_9$ | 0 | OCF$_3$ | H | F |
| n-C$_4$H$_9$ | 0 | OCF$_3$ | F | F |
| n-C$_5$H$_{11}$ | 0 | OCF$_3$ | H | H $\Delta\epsilon$ = 20.0; $\Delta n$ = 0.171 |
| n-C$_5$H$_{11}$ | 0 | OCF$_3$ | H | F |
| n-C$_5$H$_{11}$ | 0 | OCF$_3$ | F | F |
| n-C$_6$H$_{13}$ | 0 | OCF$_3$ | H | H |
| n-C$_6$H$_{13}$ | 0 | OCF$_3$ | H | F |
| n-C$_6$H$_{13}$ | 0 | OCF$_3$ | F | F |
| CH$_2$=CH | 0 | OCF$_3$ | H | H |
| CH$_2$=CH | 0 | OCF$_3$ | H | F |
| CH$_2$=CH | 0 | OCF$_3$ | F | F |
| CH$_3$CH=CH | 0 | OCF$_3$ | H | H |
| CH$_3$CH=CH | 0 | OCF$_3$ | H | F |
| CH$_3$CH=CH | 0 | OCF$_3$ | F | F |
| CH$_2$=CHC$_2$H$_4$ | 0 | OCF$_3$ | H | H |
| CH$_2$=CHC$_2$H$_4$ | 0 | OCF$_3$ | H | F |
| CH$_2$=CHC$_2$H$_4$ | 0 | OCF$_3$ | F | F |
| CH$_3$CH=CHC$_2$H$_4$ | 0 | OCF$_3$ | H | H |
| CH$_3$CH=CHC$_2$H$_4$ | 0 | OCF$_3$ | H | F |
| CH$_3$CH=CHC$_2$H$_4$ | 0 | OCF$_3$ | F | F |
| CH$_3$O | 0 | OCF$_3$ | H | H |
| CH$_3$O | 0 | OCF$_3$ | H | F |
| CH$_3$O | 0 | OCF$_3$ | F | F |
| CH$_3$ | 0 | OCHF$_2$ | H | H |
| CH$_3$ | 0 | OCHF$_2$ | H | F |
| CH$_3$ | 0 | OCHF$_2$ | F | F |
| C$_2$H$_5$ | 0 | OCHF$_2$ | H | H |
| C$_2$H$_5$ | 0 | OCHF$_2$ | H | F |
| C$_2$H$_5$ | 0 | OCHF$_2$ | F | F |
| n-C$_3$H$_7$ | 0 | OCHF$_2$ | H | H |
| n-C$_3$H$_7$ | 0 | OCHF$_2$ | H | F |
| n-C$_3$H$_7$ | 0 | OCHF$_2$ | F | F |
| n-C$_4$H$_9$ | 0 | OCHF$_2$ | H | H |
| n-C$_4$H$_9$ | 0 | OCHF$_2$ | H | F |
| n-C$_4$H$_9$ | 0 | OCHF$_2$ | F | F |
| n-C$_5$H$_{11}$ | 0 | OCHF$_2$ | H | H |
| n-C$_5$H$_{11}$ | 0 | OCHF$_2$ | H | F |
| n-C$_5$H$_{11}$ | 0 | OCHF$_2$ | F | F |
| n-C$_6$H$_{13}$ | 0 | OCHF$_2$ | H | H |
| n-C$_6$H$_{13}$ | 0 | OCHF$_2$ | H | F |
| n-C$_6$H$_{13}$ | 0 | OCHF$_2$ | F | F |
| CH$_2$=CH | 0 | OCHF$_2$ | H | H |
| CH$_2$=CH | 0 | OCHF$_2$ | H | F |
| CH$_2$=CH | 0 | OCHF$_2$ | F | F |
| CH$_3$CH=CH | 0 | OCHF$_2$ | H | H |
| CH$_3$CH=CH | 0 | OCHF$_2$ | H | F |
| CH$_3$CH=CH | 0 | OCHF$_2$ | F | F |
| CH$_2$=CHC$_2$H$_4$ | 0 | OCHF$_2$ | H | H |
| CH$_2$=CHC$_2$H$_4$ | 0 | OCHF$_2$ | H | F |
| CH$_2$=CHC$_2$H$_4$ | 0 | OCHF$_2$ | F | F |
| CH$_3$CH=CHC$_2$H$_4$ | 0 | OCHF$_2$ | H | H |
| CH$_3$CH=CHC$_2$H$_4$ | 0 | OCHF$_2$ | H | F |
| CH$_3$CH=CHC$_2$H$_4$ | 0 | OCHF$_2$ | F | F |
| CH$_3$O | 0 | OCHF$_2$ | H | H |
| CH$_3$O | 0 | OCHF$_2$ | H | F |
| CH$_3$O | 0 | OCHF$_2$ | F | F |
| CH$_3$ | 0 | CN | H | H |
| CH$_3$ | 0 | CN | H | F |
| CH$_3$ | 0 | CN | F | F |
| C$_2$H$_5$ | 0 | CN | H | H |
| C$_2$H$_5$ | 0 | CN | H | F |

-continued

| R | n | Y | L¹ | L² |
|---|---|---|---|---|
| C₂H₅ | 0 | CN | F | F |
| n-C₃H₇ | 0 | CN | H | H |
| n-C₃H₇ | 0 | CN | H | F |
| n-C₃H₇ | 0 | CN | F | F |
| n-C₄H₉ | 0 | CN | H | H |
| n-C₄H₉ | 0 | CN | H | F |
| n-C₄H₉ | 0 | CN | F | F |
| n-C₅H₁₁ | 0 | CN | H | H |
| n-C₅H₁₁ | 0 | CN | H | F |
| n-C₅H₁₁ | 0 | CN | F | F |
| n-C₆H₁₃ | 0 | CN | H | H |
| n-C₆H₁₃ | 0 | CN | H | F |
| n-C₆H₁₃ | 0 | CN | F | F |
| CH₂=CH | 0 | CN | H | H |
| CH₂=CH | 0 | CN | H | F |
| CH₂=CH | 0 | CN | F | F |
| CH₃CH=CH | 0 | CN | H | H |
| CH₃CH=CH | 0 | CN | H | F |
| CH₃CH=CH | 0 | CN | F | F |
| CH₂=CHC₂H₄ | 0 | CN | H | H |
| CH₂=CHC₂H₄ | 0 | CN | H | F |
| CH₂=CHC₂H₄ | 0 | CN | F | F |
| CH₃CH=CHC₂H₄ | 0 | CN | H | H |
| CH₃CH=CHC₂H₄ | 0 | CN | H | F |
| CH₃CH=CHC₂H₄ | 0 | CN | F | F |
| CH₃O | 0 | CN | H | H |
| CH₃O | 0 | CN | H | F |
| CH₃O | 0 | CN | F | F |

Mixture Examples

Example A

| CCH-35 | 5.0% | Clearing point: | +72.5° C. |
|---|---|---|---|
| CCP-2F.F.F | 10.0% | Δn [589 nm, 20° C.]: | +0.0902 |
| CCP-3F.F.F | 9.0% | Δε [1 kHz, 20° C.]: | +12.7 |
| CCP-3OCF₃ | 8.0% | γ₁ [mPas · s, 20° C.]: | 167 |
| CCP-4OCF₃ | 4.0% | d · Δn [μm, 20° C.]: | 0.50 |
| CGU-2-F | 11.0% | Twist [°]: | 90 |
| CGU-3-F | 9.0% | V₁₀,₀,₂₀ [V]: | 1.02 |
| CCZU-2-F | 5.0% | V₀ [V]: | 0.85 |
| CCZU-3-F | 15.0% | | |
| CCZU-5-F | 4.0% | | |
| CGIZU-3-F | 20.0% | | |

Example B

| PCH-5F | 3.19% | Δε [1 kHz, 20° C.]: | +10.5 |
|---|---|---|---|
| CCP-2OCF₂.F.F | 17.01% | V₀ [V]: | 1.11 |
| CCP-3OCF₂.F.F | 15.97% | | |
| CCP-5OCF₂.F.F | 17.01% | | |
| CUP-2F.F | 5.35% | | |
| CUP-3F.F | 5.35% | | |
| CBC-33F | 5.35% | | |
| CBC-53F | 5.35% | | |
| CBC-55F | 5.27% | | |
| CGIZU-3-F | 20.15% | | |

Example C

| BCH-3F.F | 10.82% | γ₁ [mPa · s, 20° C.]: | 142 |
|---|---|---|---|
| BCH-5F.F | 9.02% | | |
| ECCP-3OCF₃ | 4.51% | | |
| ECCP-5OCF₃ | 4.51% | | |
| CBC-33F | 1.80% | | |
| CBC-53F | 1.80% | | |
| CBC-55F | 1.80% | | |
| PCH-6F | 7.21% | | |
| PCH-7F | 5.41% | | |
| CCP-2OCF₃ | 7.21% | | |
| CCP-3OCF₃ | 10.82% | | |
| CCP-4OCF₃ | 6.31% | | |
| CCP-5OCF₃ | 9.92% | | |
| PCH-5F | 9.02% | | |
| CGIZU-3-F | 9.83% | | |

Example D

| BCH-3F.F | 10.77% | Δn [589 nm, 20° C.]: | +0.0989 |
|---|---|---|---|
| BCH-5F.F | 8.98% | Δε [1 kHz, 20° C.]: | +6.2 |
| ECCP-3OCF₃ | 4.49% | | |
| ECCP-5OCF₃ | 4.49% | | |
| CBC-33F | 1.80% | | |
| CBC-53F | 1.80% | | |
| CBC-55F | 1.80% | | |
| PCH-6F | 7.18% | | |
| PCH-7F | 5.39% | | |
| CCP-2OCF₃ | 7.18% | | |
| CCP-3OCF₃ | 10.77% | | |
| CCP-4OCF₃ | 6.28% | | |
| CCP-5OCF₃ | 9.87% | | |
| PCH-5F | 8.98% | | |
| CGIZU-3-F | 10.23% | | |

What is claimed is:

1. A liquid-crystalline ester compound of the formula I

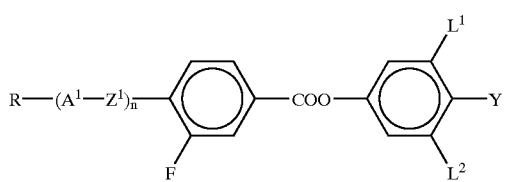

in which

R is an alkyl or alkenyl radical having 1 to 15 carbon atoms which is unsubstituted, monosubstituted by CN or $CF_3$ or monosubstituted to perhalosubstituted by halogen, where one or more $CH_2$ groups in these radicals, in each case independently of one another, are optionally replaced by —O—, —S—,

—CO—, —CO—O—, —O—CO— or —O—CO—O— in such a way that O atoms are not linked directly to one another, $A^1$ (a) is a trans-1,4-cyclohexylene radical in which, one or more non-adjacent $CH_2$ groups are optionally replaced by —O— and/or —S—, (b) is a 1,4-phenylene radical, in which, in addition, one or two CH groups may be replaced by N, (c) is a 1,4-cyclohexenylene radical, (d) is a radical selected from the group consisting of 1,4-bicyclo[2.2.2]-octylene, piperidine-1,4-diyl, naphthalene-2,6-diyl, decahydronaphthalene-2,6-diyl and 1,2,3,4-tetrahydronaphthalene-2,6-diyl, where the radicals (a), (b), (c) and (d) are optionally monosubstituted or polysubstituted by CN or fluorine, $Z^1$ is —COO—, —O—CO—, —CH$_2$O—, —OCH$_2$—, —C$_2$H$_4$—, —CH=CH—, —CF$_2$O—, —OCF$_2$—, —C≡C—, —(CH$_2$)$_4$—, —CH=CHC$_2$H$_4$—, —C$_2$F$_4$— or a single bond, $L^1$ or $L^2$ are each, independently of one another, H or F, Y is F, Cl, CN or an alkyl or alkoxy radical having 1 to 6 carbon atoms which is substituted by one or more halogen atoms, where one or more CH$_2$ groups are optionally replaced by —O— or —CH=CH— in such a way that O atoms are not linked directly to one another, and n is 0, 1 or 2, provided that, when Y=CN, $L^1$ and/or $L^2$ is F.

2. An ester compound according to claim 1, wherein $A^1$ is a trans-1,4-cyclohexylene radical, n=1 and $Z^1$=single bond.

3. An ester compound according to claim 1 wherein $L^1$ and/or $L^2$ are F.

4. An ester compound according to claim 1, wherein $Z^1$ is a single bond.

5. An ester compound according to claim 1, wherein Y is F, CN, OCF$_3$ or OCHF$_2$.

6. A liquid-crystalline medium comprising at least one ester compound of claim 1.

7. A liquid-crystalline medium based on a mixture of polar compounds having positive dielectric anisotropy, which comprises one or more compounds of the formula I of claim 1 and additionally one or more compounds selected from the group consisting of compounds of the formulae II, III, IV, V, VI, VII and VIII:

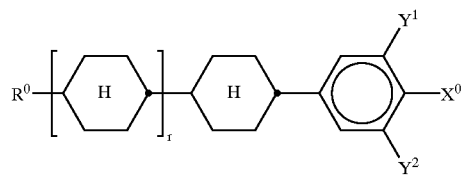

II

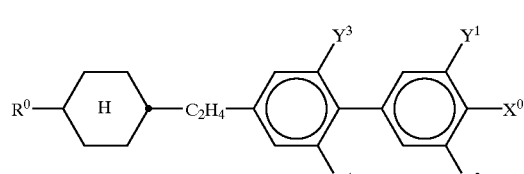

III

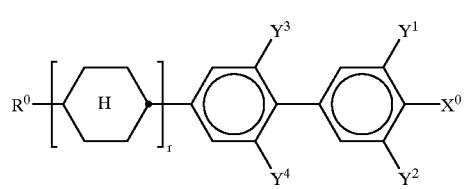

IV

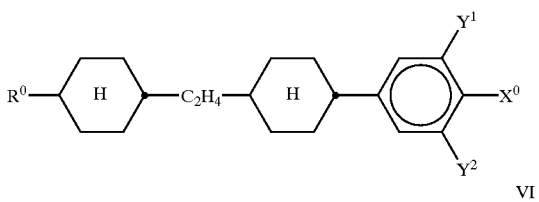

V

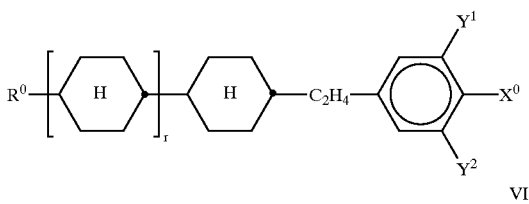

VI

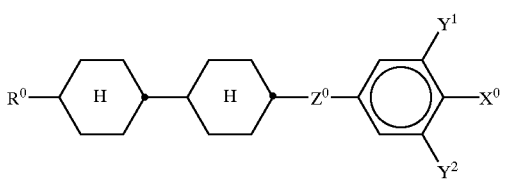

VII

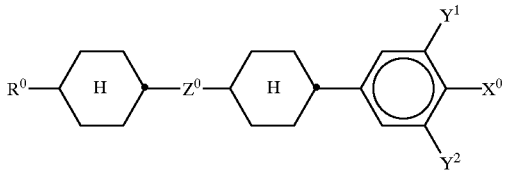

VIII in which the individual radicals have the following meanings:

$R^0$ is n-alkyl, oxaalkyl, fluoroalkyl or alkenyl, in each case having 1 to 9 carbon atoms, $X^0$ is F, Cl, or halogenated alkyl, alkenyl or alkoxy having 1 to 6 carbon atoms, $Z^0$ is —C$_4$H$_8$—, —CF$_2$O—, —OCF$_2$—, —C$_2$F$_4$— or —CH=CH—, $Y^1$ to $Y^4$ are each, independently of one another, H or F, r is 0 or 1.

8. A liquid-crystalline medium according to claim 7, wherein the proportion of compounds of the formulae I to VIII together in the total mixture is at least 50% by weight.

9. A liquid-crystalline medium according to claim 7, wherein the proportion of compounds of the formula I in the total mixture is from 5 to 50% by weight.

10. A liquid-crystalline medium according to claim 7, wherein the proportion of compounds of the formulae II to VIII in the total mixture is from 20 to 80% by weight.

11. A liquid-crystalline medium according to claim 7, which additionally comprises one or more compounds of the formula E1

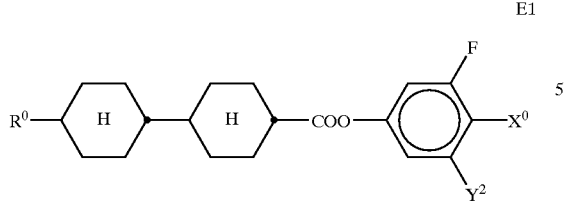

in which R⁰, X⁰ and y² are as defined in claim 7.

12. A liquid-crystalline medium according to claim 11, wherein for formula E1 X⁰ is F or OCF₃ and Y² is H or F.

13. A liquid-crystalline medium according to claim 7, which additionally comprises one or more compounds of the formula IVa

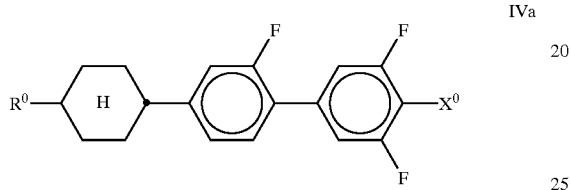

in which R⁰ and X⁰ are as defined in claim 7.

14. A liquid-crystalline medium according to claim 7, wherein the compound of the formula I is selected from the group consisting of compounds of formulas Ia to Ik:

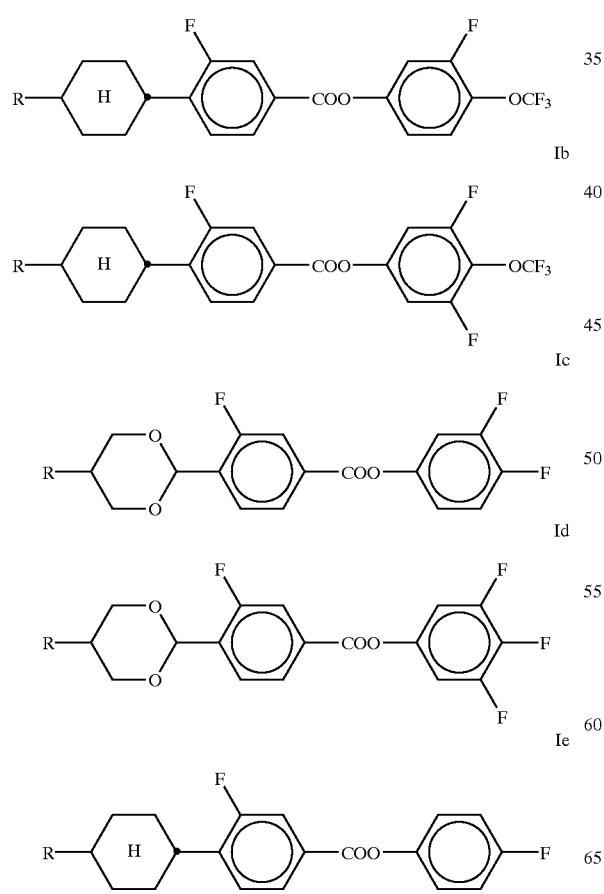

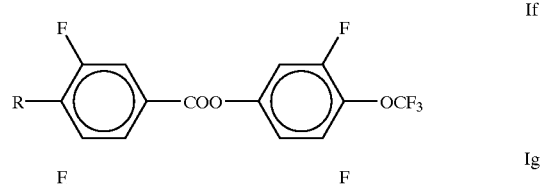

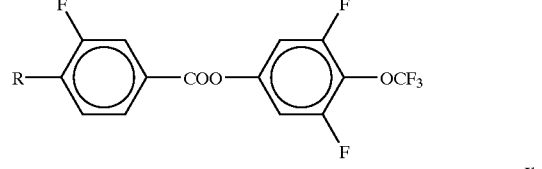

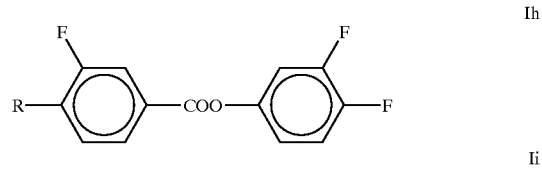

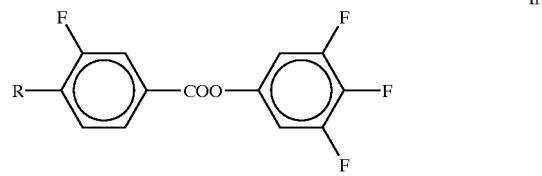

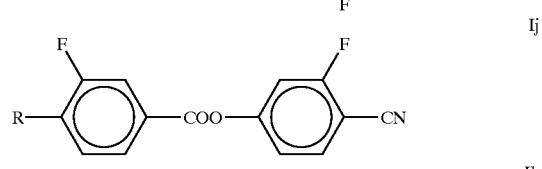

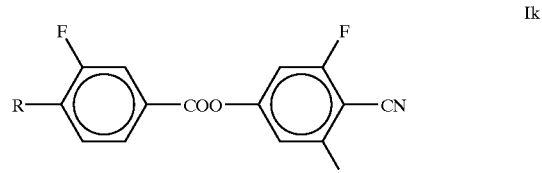

where R is as defined.

15. An electro-optical device comprising a liquid-crystalline medium according to claim 7.

16. An electro-optical liquid-crystal display containing a liquid-crystalline medium according to claim 7.

17. A liquid-crystalline medium according to claim 7 which maintains a nematic phase down to −20° C., has a clearing point above 70° C., a birefringence of ≦0.1 and a threshold voltage of about 1.5V or less.

18. An ester compound of claim 1, wherein n is 1 or 2 and Z¹ is —CH₂—CH₂— or a single bond.

19. A liquid crystalline medium of claim 7, wherein the medium comprises at least one compound of the formulae II, III and/or IV in which X⁰ is F, OCF₃, OCHF₂, F, OCH=CF₂, OCF=CF₂ or OCF₂—CF₂H.

20. A liquid crystalline medium of claim 7, wherein the medium consists essentially of compounds of the formula I and compounds of the formulae II, III, IV, V, VI, VII and VIII.

* * * * *